US012653842B2

(12) United States Patent (10) Patent No.: US 12,653,842 B2
Noh et al. (45) Date of Patent: \*Jun. 16, 2026

(54) TREATMENT OF INTERVERTEBRAL DISC DEGENERATION

(71) Applicant: Kolon Tissuegene, Inc., Rockville, MD (US)

(72) Inventors: Moon Jong Noh, Rockville, MD (US); Hyun Bae, Rockville, MD (US); Sung Woo Kang, Rockville, MD (US); Kwan Hee Lee, Rockville, MD (US)

(73) Assignee: KOLON TISSUEGENE, INC, Rockville, MD (US)

( \* ) Notice: Subject to any disclaimer, the term of this patent is extended or adjusted under 35 U.S.C. 154(b) by 1148 days.

This patent is subject to a terminal disclaimer.

(21) Appl. No.: 17/599,831

(22) PCT Filed: Mar. 30, 2020

(86) PCT No.: PCT/US2020/025705

§ 371 (c)(1),
(2) Date: Sep. 29, 2021

(87) PCT Pub. No.: WO2020/205730

PCT Pub. Date: Oct. 8, 2020

(65) Prior Publication Data

US 2022/0160834 A1 May 26, 2022

Related U.S. Application Data

(60) Provisional application No. 62/826,676, filed on Mar. 29, 2019.

(51) Int. Cl.
| | |
|---|---|
| *A61K 35/35* | (2015.01) |
| *A61K 9/00* | (2006.01) |
| *A61K 35/22* | (2015.01) |
| *A61K 35/32* | (2015.01) |
| *A61K 35/36* | (2015.01) |
| *A61K 38/18* | (2006.01) |
| *A61P 19/02* | (2006.01) |
| *A61P 19/04* | (2006.01) |
| *A61P 19/08* | (2006.01) |

(52) U.S. Cl.
CPC .............. *A61K 35/35* (2013.01); *A61K 35/22* (2013.01); *A61K 35/32* (2013.01); *A61K 35/36* (2013.01); *A61K 38/1841* (2013.01); *A61P 19/02* (2018.01); *A61P 19/04* (2018.01); *A61P 19/08* (2018.01); *A61K 9/0019* (2013.01)

(58) Field of Classification Search
CPC ................................. A61K 35/32; A61K 35/35
See application file for complete search history.

(56) References Cited

U.S. PATENT DOCUMENTS

| | | | |
|---|---|---|---|
| 6,150,163 | A | 11/2000 | McPherson et al. |
| 6,479,066 | B1 | 11/2002 | Harpstead |
| 7,005,127 | B2 | 2/2006 | Song et al. |
| 7,338,655 | B1 | 3/2008 | Noh et al. |
| 2003/0175257 | A1 | 9/2003 | Song et al. |
| 2003/0185809 | A1 | 10/2003 | Song et al. |
| 2003/0225021 | A1 | 12/2003 | McKay et al. |
| 2005/0031666 | A1 | 2/2005 | Trieu |
| 2006/0115463 | A1 | 6/2006 | Song et al. |
| 2006/0160214 | A1 | 7/2006 | Masuda et al. |
| 2006/0275273 | A1 | 12/2006 | Seyedin et al. |
| 2006/0292131 | A1 | 12/2006 | Binette et al. |
| 2007/0128174 | A1 | 6/2007 | Kleinsek et al. |
| 2008/0075703 | A1 | 3/2008 | Song et al. |
| 2009/0238806 | A1 | 9/2009 | Noh et al. |
| 2010/0015129 | A1 | 1/2010 | Abramson et al. |
| 2010/0055080 | A1 | 3/2010 | Song et al. |
| 2010/0316612 | A1 | 12/2010 | Noh et al. |
| 2010/0330053 | A1 | 12/2010 | Song et al. |
| 2011/0189138 | A1 | 8/2011 | Ghosh |
| 2014/0099709 | A1 | 4/2014 | Presnell et al. |
| 2016/0220699 | A1 | 8/2016 | O'Heeron |
| 2018/0238475 | A1 | 8/2018 | Zumbrum |
| 2018/0264045 | A1 | 9/2018 | Choi et al. |
| 2022/0160780 | A1 | 5/2022 | Noh et al. |
| 2022/0249573 | A1 | 8/2022 | Noh et al. |
| 2023/0256025 | A1 | 8/2023 | Noh et al. |
| 2023/0256055 | A1 | 8/2023 | Noh et al. |
| 2025/0090635 | A1 | 3/2025 | Noh et al. |

FOREIGN PATENT DOCUMENTS

| | | |
|---|---|---|
| CA | 2 744 445 A1 | 6/2010 |
| CN | 1295617 A | 5/2001 |
| CN | 1371289 A | 9/2002 |
| CN | 1589905 A | 3/2005 |

(Continued)

OTHER PUBLICATIONS

Luo et al. Evaluation of Percutaneous Intradiscal Amniotic Suspension Allograft in a Rabbit Model of Intervertebral Disc Degeneration. Spine 2018, 44;6:E329-E337. (Year: 2018).*
Bossolasco et al. Molecular and phenotypic characterization of human amniotic fluid cells and their differentiation potential. Cell Research 2006, 16:329-336. (Year: 2006).*
Javad Parvizi, et al. "Chapter 7: Bearing Surface Materials for Hip, Knee, and Spinal Disk Replacement", Section 1: Principles of Orthopaedics, Orthopaedic Knowledge, 2011, Update 10, pp. 73-83 (11 pages total).

(Continued)

*Primary Examiner* — Christopher M Babic
*Assistant Examiner* — Jennifer S Spence
(74) *Attorney, Agent, or Firm* — Sughrue Mion, PLLC

(57) ABSTRACT

The present application discloses a method for preventing or retarding degeneration of intervertebral disc at an intervertebral disc defect site, which includes injecting a mammalian connective tissue cell into the intervertebral disc defect site.

11 Claims, 18 Drawing Sheets

(56) References Cited

FOREIGN PATENT DOCUMENTS

| CN | 1653179 A | 8/2005 |
|---|---|---|
| CN | 1655798 A | 8/2005 |
| CN | 101085357 A | 12/2007 |
| CN | 101748095 A | 6/2010 |
| CN | 103087992 A | 5/2013 |
| CN | 105209607 A | 12/2015 |
| CN | 107405388 A | 11/2017 |
| JP | 2002-542801 A | 12/2002 |
| JP | 2005-519698 A | 7/2005 |
| JP | 2005-521732 A | 7/2005 |
| JP | 2009-137980 A | 6/2009 |
| JP | 2009-540826 A | 11/2009 |
| JP | 2011-515418 A | 5/2011 |
| JP | 2012-509942 A | 4/2012 |
| JP | 2016531147 A | 10/2016 |
| RU | 2 576 447 C2 | 3/2016 |
| WO | 99/31221 A1 | 6/1999 |
| WO | 00/66177 A1 | 11/2000 |
| WO | 02/074345 A2 | 9/2002 |
| WO | 03/083079 A2 | 10/2003 |
| WO | 03/083080 A2 | 10/2003 |
| WO | 2005/081870 A2 | 9/2005 |
| WO | 2006/015304 A2 | 2/2006 |
| WO | 2006/128100 A2 | 11/2006 |
| WO | 2007/035843 A2 | 3/2007 |
| WO | 2009/117740 A2 | 9/2009 |
| WO | 2010/068510 A1 | 6/2010 |
| WO | 2016/126139 A1 | 8/2016 |
| WO | 2018/135902 A1 | 7/2018 |
| WO | 2020/205720 A2 | 10/2020 |

OTHER PUBLICATIONS

MatežGorensek, et al., "Nucleus Pulposus Repair With Cultured Autologous Elastic Cartilage Derived Chondrocytes", Cellular and Molecular Biology Letters, 2004; vol. 9, pp. 363-373 (11 pages total).
Yejia Zhang, et al., "4:28 98. Chondrocyte Based Gene Therapy for the Degenerating Intervertebral Disc in the Rabbit Disc Organ Culture System", Proceedings of the NASS 21st Annual Meeting / The Spine Journal, vol. 6, 2006, p. 48s (1 page total).
Xu Li, et al., "Increased Synthesis of Extracellular Matrix in Passaged Nucleus Pulposus Cells By Transfection With Adenoviral Vectors Containing Human Transforming Growth Factor ß1." Chinese Journal of Reparative and Reconstructive Surgery, Dec. 2007, vol. 21, No. 12, pp. 1342-1347 (6 pages total).
Koichi Masuda, et al., "Growth factors and the intervertebral disc", The Spine Journal, 2004, vol. 4, pp. 330S-340S (11 pages total).
Orthopedic Surgery, Restorative Surgery (Seikei Geka), vol. 54, No. 1 (2003-1), p. 52 (5 pages total).
Kimiaki Sato, et al., "Experimental Intradiscal Drug Injection: Histological Studies and Measurement of Intradiscal Pressure", Orthopedic Surgery and Traumatology, 1996, 45(1) pp. 123-126 (4 pages total).
Bosserhoff, et al., Biomaterials, 2003, vol. 24, p. 3229-3234 (Abstract, 1 page total).
International Search Report for PCT/US2020/025705 dated Jul. 1, 2020.
Final Office Action issued Jul. 22, 2022 in U.S. Appl. No. 12/409,311.
Tom Hodgkinson, et al., "Therapeutic potential of growth differentiation factors in the treatment of degenerative disc diseases", JOR Spine, 2019, vol. 2, e1045, pp. 1-15 (15 pages total).
S. Chen, et al., "TGF-ß signaling in intervertebral disc health and disease", Osteoarthritis and Cartilage, 2019, vol. 27, pp. 1109-1117 (9 pages total).
Justin C. Kennon, et al., "Current insights on use of growth factors as therapy for Intervertebral Disc Degeneration", BioMol Concepts, 2018, vol. 9, pp. 43-52 (10 pages total).
Office Action issued Apr. 25, 2023 in U.S. Appl. No. 17/092,712.
Office Action issued Sep. 25, 2023 in U.S. Appl. No. 12/409,311.

James A. Martin, et al., "Age-Related Decline in Chondrocyte Response to Insulin-Like Growth Factor-I: The Role of Growth Factor Binding Proteins", Journal of Orthopaedic Research, 1997, vol. 15, pp. 491-498 (8 pages total).
Javed Iqbal, et al., "Age-Related Effects of TGF-ß on Proteoglycan Synthesis in Equine Articular Cartilage", Biochemical and Biophysical Research Communications, 2000, vol. 274, pp. 467-471 (5 pages total).
Nicolas Tran-Khanh, et al., "Aged bovine chondrocytes display a diminished capacity to produce a collagen-rich, mechanically functional cartilage extracellular matrix", Journal of Orthopaedic Research, 2005, vol. 23, pp. 1354-1362 (9 pages total).
Office Action issued Feb. 15, 2024 in U.S. Appl. No. 12/409,311.
Office Action issued Oct. 6, 2023 in U.S. Appl. No. 17/092,712.
Philip Thomas, et al., "HEK293 cell line: A vehicle for the expression of recombinant proteins", Journal of Pharmacological and Toxicological Methods, 2005, vol. 51, pp. 187-200 (14 pages total).
Office Action issued Feb. 15, 2024 in U.S. Appl. No. 17/186,332.
Written Opinion dated Aug. 10, 2023 in Singapore Application No. 11202110844U.
Search Report dated Aug. 10, 2023 in Singapore Application No. 11202110844U.
Invitation to Respond to Written Opinion dated Aug. 14, 2023 in Singapore Application No. 11202110844U.
European Communication issued Oct. 26, 2023 in Application No. 20 784 818.5.
Office Action issued Oct. 13, 2023 in U.S. Appl. No. 17/092,779.
Hans Jörg Meisel, et al., "Clinical experience in cell-based therapeutics: Disc chondrocyte transplantation A treatment for degenerated or damaged intervertebral disc", Biomolecular Engineering, 2007, vol. 24, pp. 5-21 (17 pages total).
Koichi Masuda, et al., "Growth Factors and Treatment of Intervertebral Disc Degeneration", SPINE, 2004, vol. 29, No. 23, pp. 2757-2769 (13 pages total).
Extended European Search Report issued Dec. 8, 2022 in European Application No. 20784818.5.
Sun U. Song, Ph.D., et al., "Hyaline Cartilage Regeneration Using Mixed Human Chondrocytes and Transforming Growth Factor-ß1-Producing Chondrocytes", Tissue Engineering, 2005, vol. 11, No. 9/10, pp. 1516-1526 (11 pages total).
Dug Keun Lee, Ph.D., et al., "Continuous Transforming Growth Factor ß1 Secretion by Cell-Mediated Gene Therapy Maintains Chondrocyte Redifferentiation", Tissue Engineering, 2005, vol. 11, No. 1/2, pp. 310-318 (9 pages total).
Sun U. Song, Ph.D., et al., "Regeneration of Hyaline Articular Cartilage with Irradiated Transforming Growth Factor ß1-Producing Fibroblasts", Tissue Engineering, 2004, vol. 10, No. 5-6, pp. 665-672 (9 pages total).
Communication dated Aug. 20, 2024 issued by the Japanese Patent Office in application No. 2021-560195.
Kelly L. Walton, et al., "Two Distinct Regions of Latency-associated Peptide Coordinate Stability of the Latent Transforming Growth Factor-ß1 Complex", The Journal of Biological Chemistry, vol. 285, No. 22, 2010, pp. 17029-17037.
Kh. V. Malysheva, et al., "Generation of Optimized Preparations of Bone Morphogenetic Proteins for Bone Regeneration", Ukraine Biochemical Journal, 2016, vol. 88, No. 6, pp. 2-12.
Communication dated Mar. 6, 2025 issued by the Japanese Patent Office in application No. 2021-560195.
Communication dated Aug. 25, 2025 in Indian Application No. P00202109357.
Communication dated Jul. 25, 2025 in Canadian Application No. 3135496.
Communication dated Jul. 31, 2025 in Saudi Arabian Application No. 521430457.
Rybakovsky, et al., "Improving Transient Transfection Efficiency in a Differentiated, Polar Epithelial Cell Layer", Journal of Biomolecular Techniques, Jul. 2019, vol. 30, pp. 19-24 (6 pages).
Communication dated Sep. 21, 2025 in Korean Application No. 10-2021-7035297.

* cited by examiner

FIG. 6A                    FIG. 6B
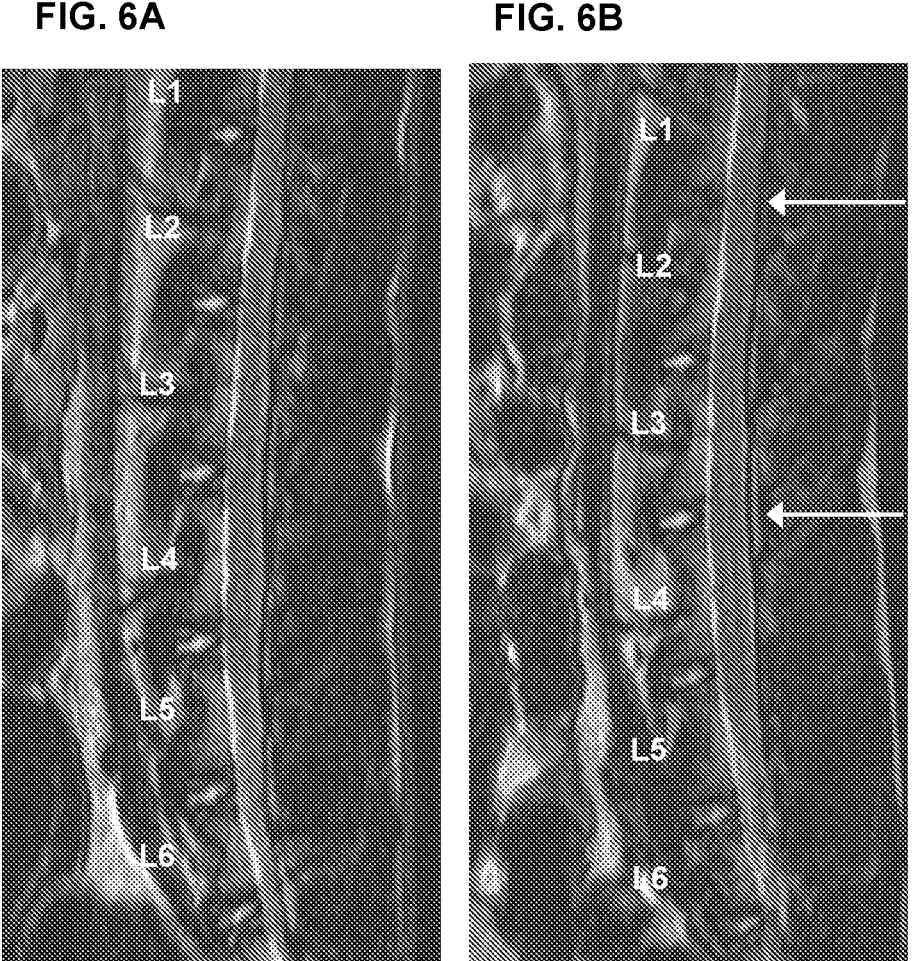

FIG. 9A                          FIG. 9B
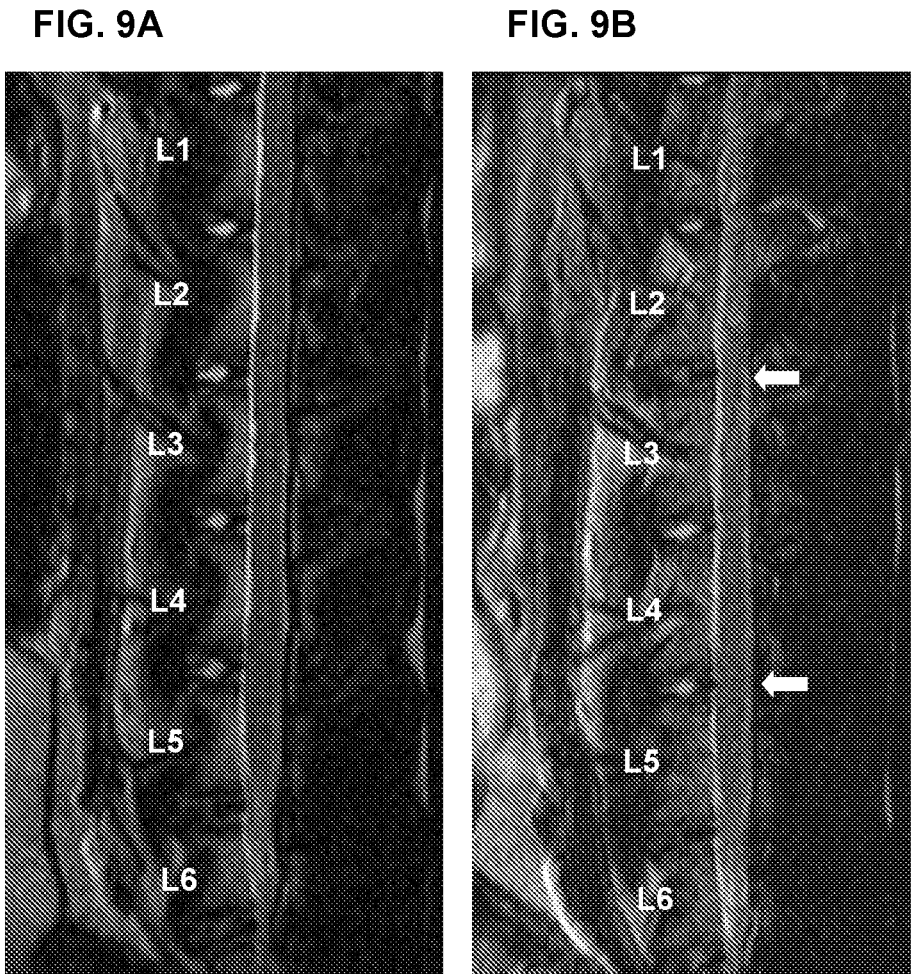

TREATMENT OF INTERVERTEBRAL DISC DEGENERATION

CROSS REFERENCE TO RELATED APPLICATIONS

This is a National Phase entry of International Application No. PCT/US2020/025705, filed Mar. 30, 2020, which claims priority to U.S. Provisional Patent Application No. 62/826, 676, filed Mar. 29, 2019, the disclosures of which are incorporated herein by reference in their entireties.

BACKGROUND OF THE INVENTION

Field of the Invention

The present invention relates to prevention or retardation of intervertebral disc degeneration. The present application also relates to treating degenerating disc by preventing or retarding intervertebral disc degeneration. The present invention also relates to methods of using chondrocytes for introduction into injured intervertebral disc region and preventing or retarding degeneration of the intervertebral disc. The present invention also relates to a method of introducing at least one gene encoding a member of the transforming growth factor β superfamily into at least one mammalian cell for use in preventing or retarding degeneration of intervertebral disc in the mammalian host. The present invention also relates to a method of using a mixture of chondrocytes and mammalian cells containing a gene encoding a member of the transforming growth factor β superfamily into injured intervertebral disc region and preventing or retarding degeneration of the intervertebral disc.

SUMMARY OF THE INVENTION

In one aspect, the present invention is directed to a method for preventing or retarding degeneration of intervertebral disc at an intervertebral disc defect site, which includes injecting a mammalian connective tissue cell into the intervertebral disc defect site. The process preferably does not use a scaffolding or any supporting structure for the cells. Preferably, non-transfected chondrocyte or fibroblast is used, and the subject is preferably a human being. If a chondrocyte is being used, the chondrocyte is preferably a non-disc chondrocyte or juvenile chondrocyte, meaning that the cells are isolated from a child who is less than two years old. In other aspects, the chondrocyte may be primed chondrocytes. In particular, the connective tissue cell may be allogeneic relative to the mammalian subject sought to be treated.

Transfected mammalian cells as discussed above may include epithelial cells, preferably human epithelial cells, or human embryonic kidney 293 cells, also referred to as HEK 293, HEK-293, or 293 cells.

In one aspect, the present invention relates to methods of using allogeneic juvenile chondrocytes or allogeneic non-disc chondrocytes for introduction into injured intervertebral disc region and preventing or retarding degeneration of the intervertebral disc.

In one aspect, the present invention is used to prevent or retard further degeneration of an area in the intervertebral disc that has been injured, torn or herniated.

In another aspect, the invention is directed to a method for preventing or retarding degeneration of intervertebral disc at an intervertebral disc defect site of a mammal, which method includes a) inserting a gene encoding a protein having intervertebral disc regenerating function into a mammalian cell, and b) transplanting the mammalian cell into the intervertebral disc defect site. The process preferably does not use a scaffolding or any supporting structure for the cells. In this method, the gene may belong to TGF-β superfamily, such as TGF-β, and preferably TGF-β1.

Transfected mammalian cells as discussed above may include epithelial cells, preferably human epithelial cells, or human embryonic kidney 293 cells, also referred to as HEK 293, HEK-293, or 293 cells.

In yet another aspect, the invention is directed to method for preventing or retarding degeneration of intervertebral disc at an intervertebral disc defect site of a mammal, which includes a) inserting a gene encoding a protein having intervertebral disc regenerating function into a first mammalian cell, and b) transplanting a mixture of the mammalian cell of a) and unmodified second mammalian connective tissue cell into the intervertebral disc defect site. The process preferably does not use a scaffolding or any supporting structure for the cells. In this method, the gene may belong to TGF-β superfamily, such as TGF-β, and preferably TGF-β1.

The first transfected mammalian cells as discussed above may include epithelial cells, preferably human epithelial cells, or human embryonic kidney 293 cells, also referred to as HEK 293, HEK-293, or 293 cells.

The second mammalian connective tissue cell may be chondrocyte or fibroblast. In the case of chondrocyte, the chondrocyte may be non-disc chondrocyte or juvenile chondrocyte. In particular, the chondrocyte for the second mammalian connective tissue cell may be a primed chondrocyte. In another aspect, either or both of the first or second connective tissue cell may be allogeneic relative to the mammalian subject or to each other.

BRIEF DESCRIPTION OF THE DRAWINGS

Figures 1D, 1E, 1F:
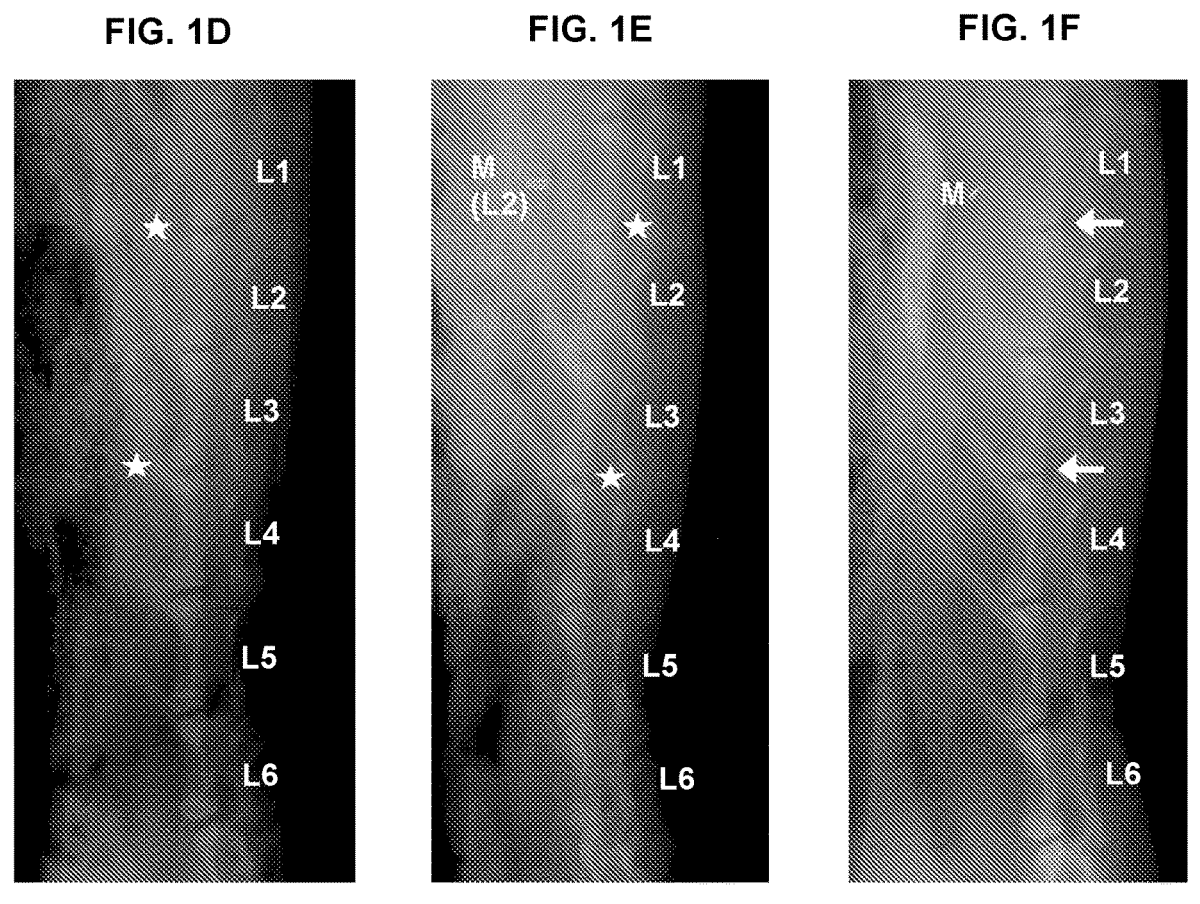

FIGS. 1A-1F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment is seen at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows MRI radiograph of a rabbit spine eight (8) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc. Mixed cell treatment in particular, has an intervertebral anti-degenerating effect.

Figures 4A, 4B:
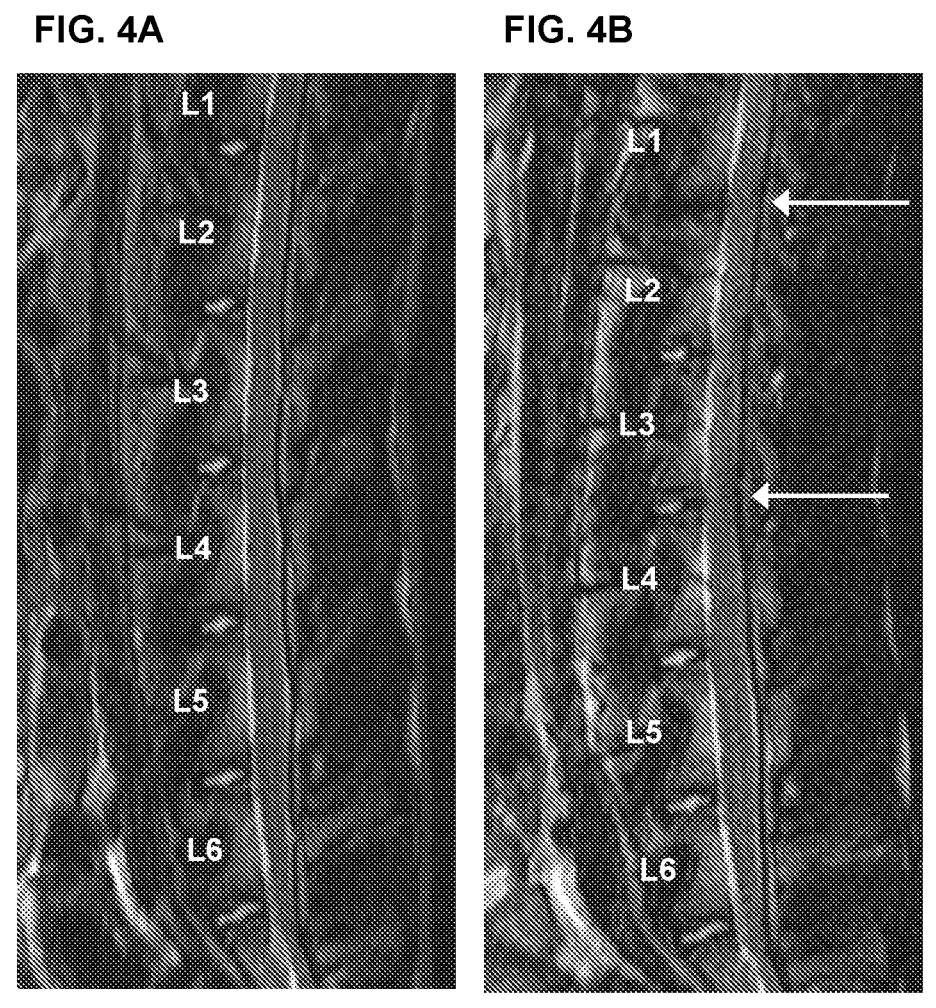

FIGS. 4A-4D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and mixture of TGF-β1-producing 293 cells and untransduced human chondrocytes in 1:3 ratio were injected, (ii) no puncture and no treatment control at spine locus L2/3, and (iii) disc at L3/4 was injured and TGF-β1-producing 293 cells were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc. TGF-β1-producing 293 cells treatment in particular, has an intervertebral anti-degenerating effect.

Figures 5C, 5D:
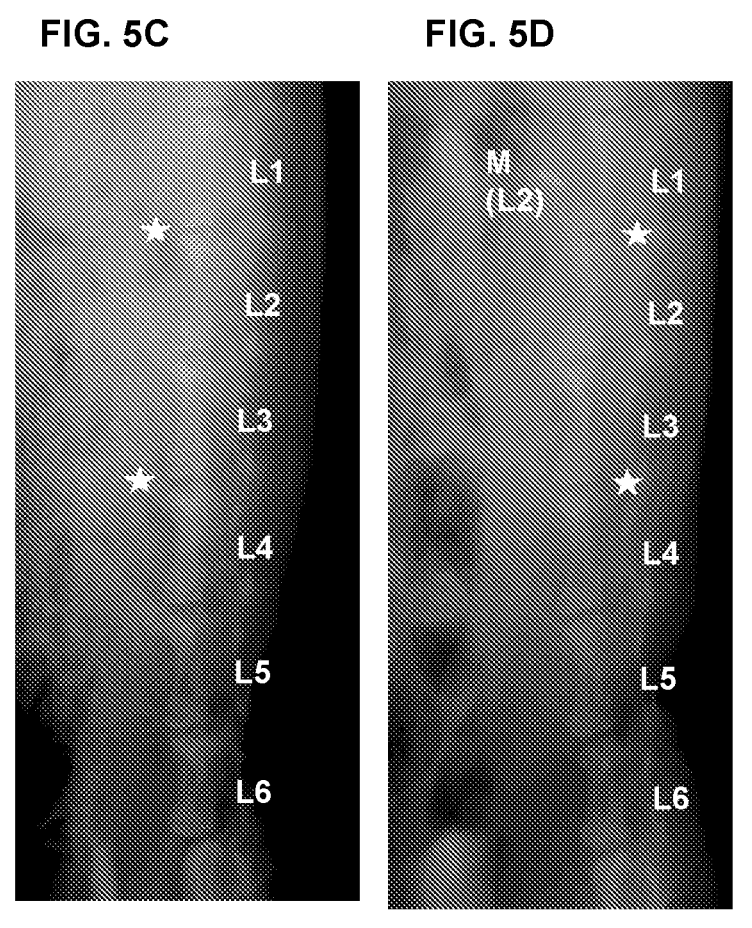

FIGS. 5A-5D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and mixture of TGF-β1-producing 293 cells and untransduced human chondrocytes in 1:3 ratio were injected, (ii) no puncture and no treatment control at spine locus L2/3, and (iii) disc at L3/4 was injured and TGF-β1-producing 293 cells were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc. TGF-β1-producing 293 cells treatment and mixed cell treatments in particular, have an intervertebral anti-degenerating effect.

Figure 6C:
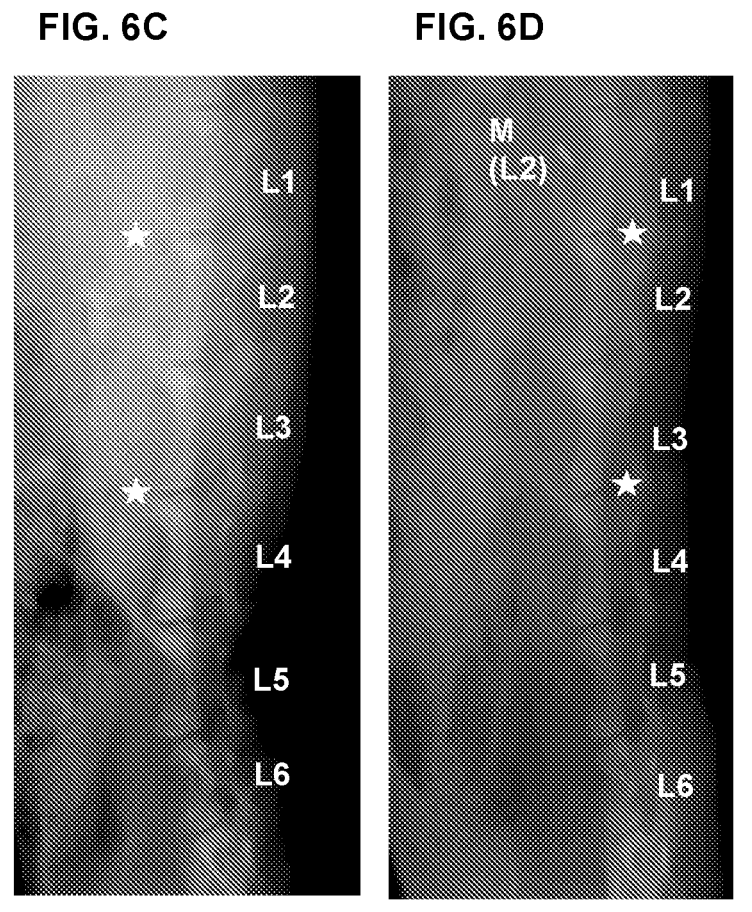

FIGS. 6A-6D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc. Untransduced chondrocytes treatment has an intervertebral anti-degenerating effect.

FIGS. 7A-7F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (C) shows MRI radiograph of a rabbit spine eight (8) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc. Untransduced chondrocytes treatment has an intervertebral anti-degenerating effect.

Figures 9C, 9D:
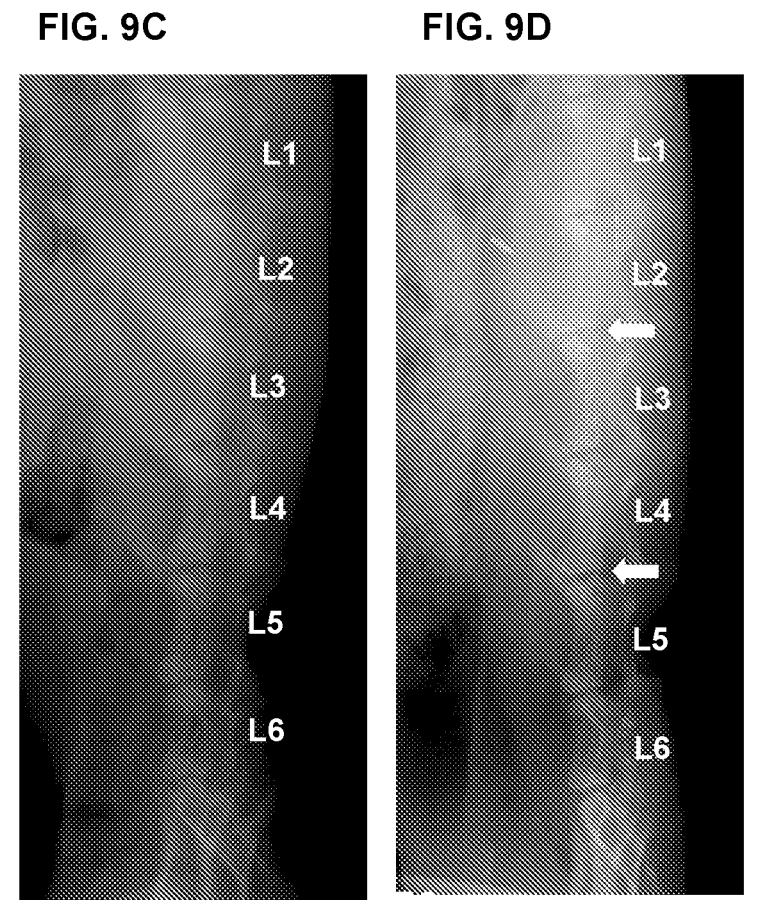

FIGS. 9A-9D show a slowing, retardation or prevention of degeneration of injured disc. (A) shows MRI radiograph of rabbit spine pre-surgery; (B) shows MRI radiograph of a rabbit spine eight (8) weeks after surgery in which (i) the disc at L2/3 was injured and cell culture media DMEM was injected, (ii) no puncture and no treatment control at spine locus L3/4, and (iii) disc at L4/5 was injured and primed chondrocytes were injected; arrows point to L2/3 and L4/5 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc. Primed chondrocyte treatment has an intervertebral anti-degenerating effect.

DETAILED DESCRIPTION OF THE INVENTION

Figures 1A, 1B, 1C:
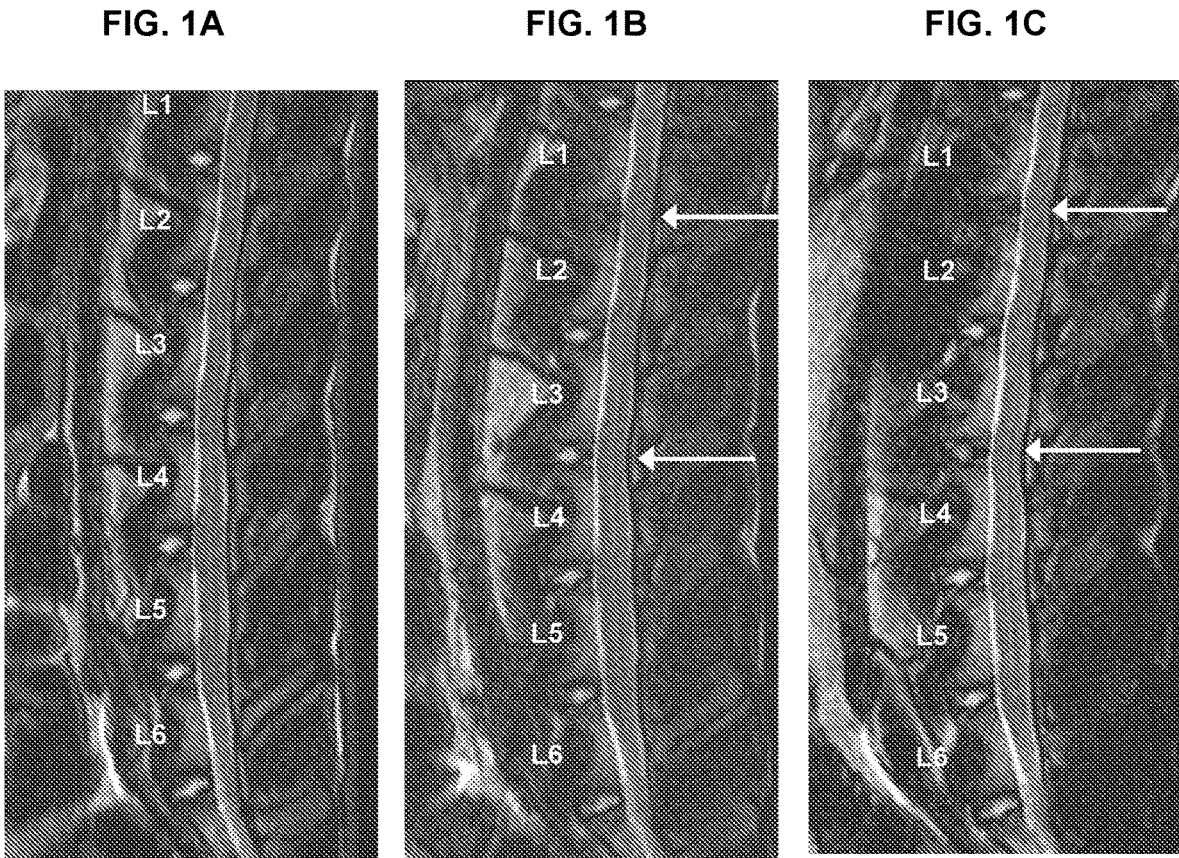
Figures 2A, 2B, 2C:
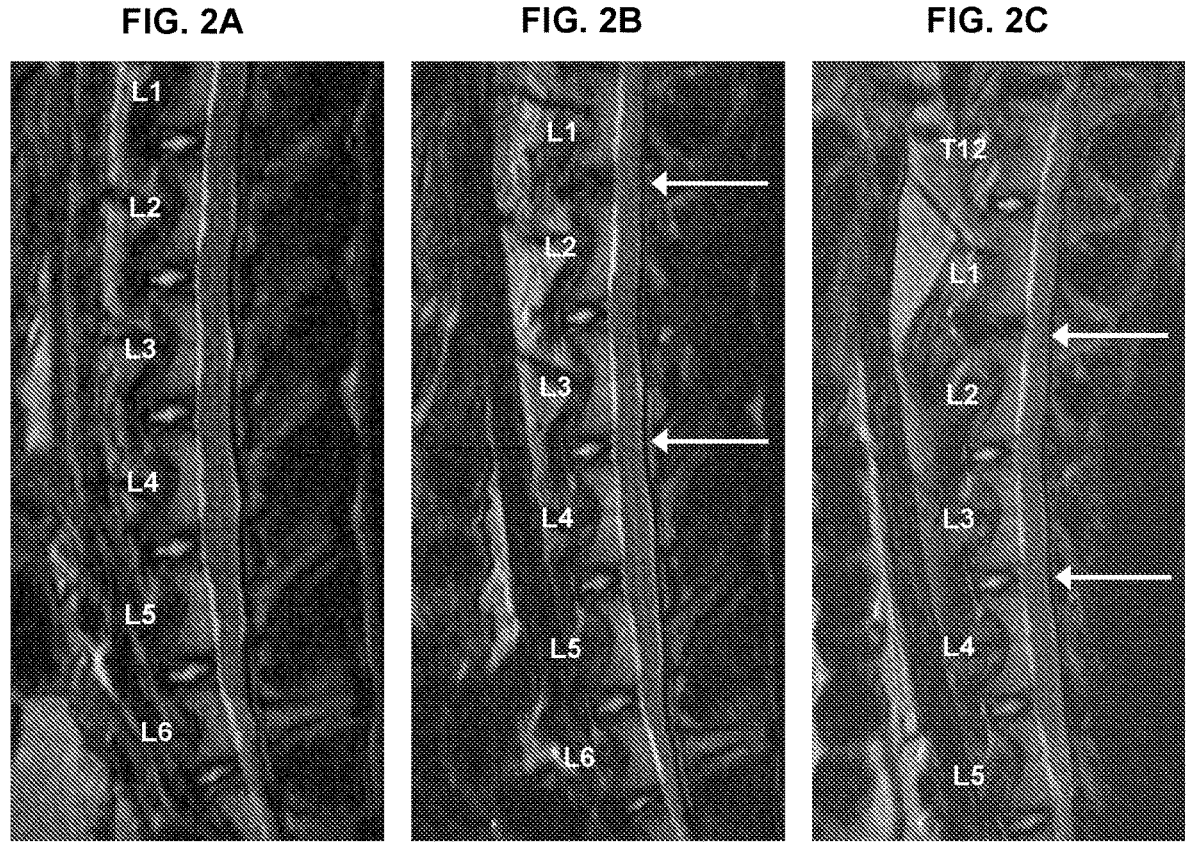
FIGS. 2A-2F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows MRI radiograph of a rabbit spine eight (8) weeks after surgery in which (i) the disc at L1/2 was injured and TGF-β1-producing 293 cells were injected, (ii) no puncture and no treatment is seen at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc. Mixed cell treatment in particular, has an intervertebral anti-degenerating effect.
Figures 2D, 2E, 2F:
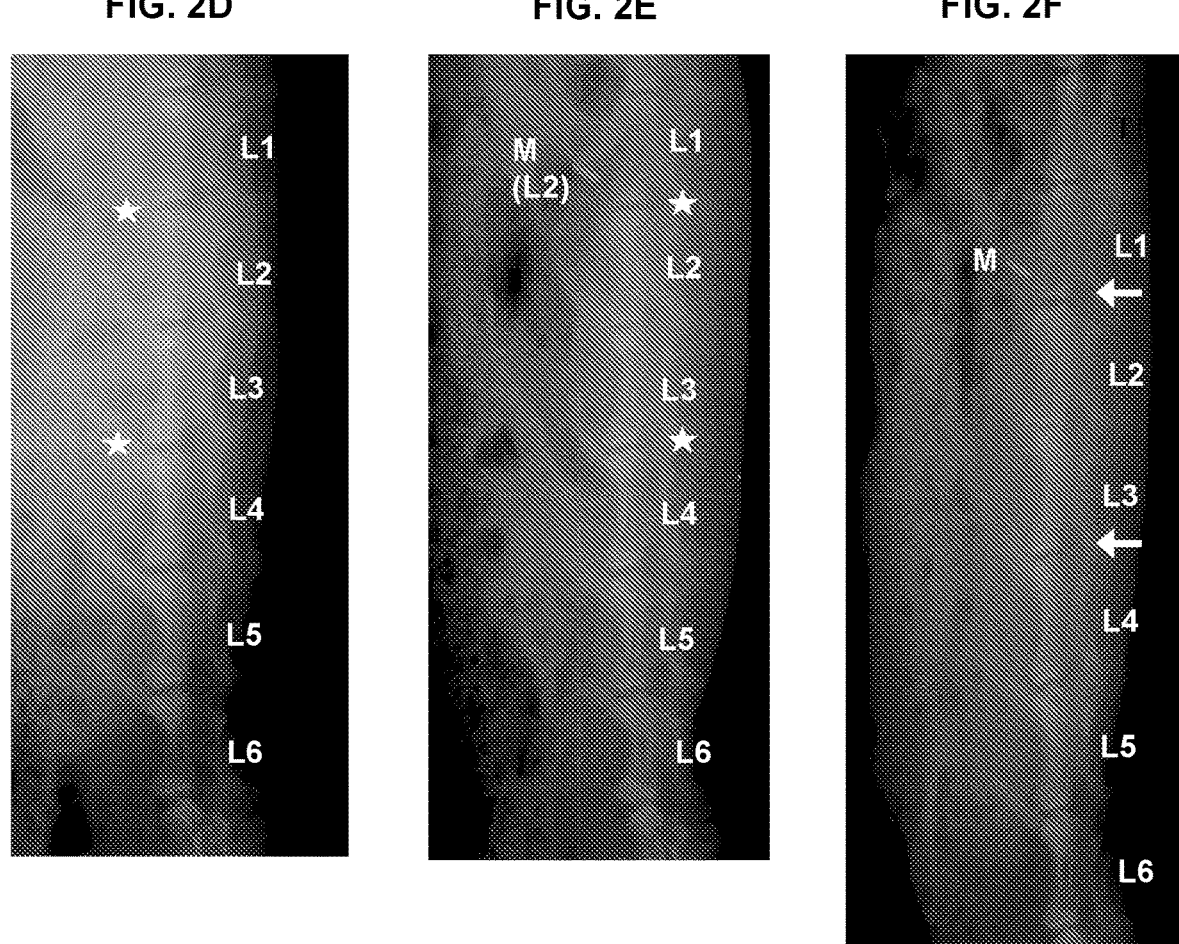
Figures 3A, 3B:
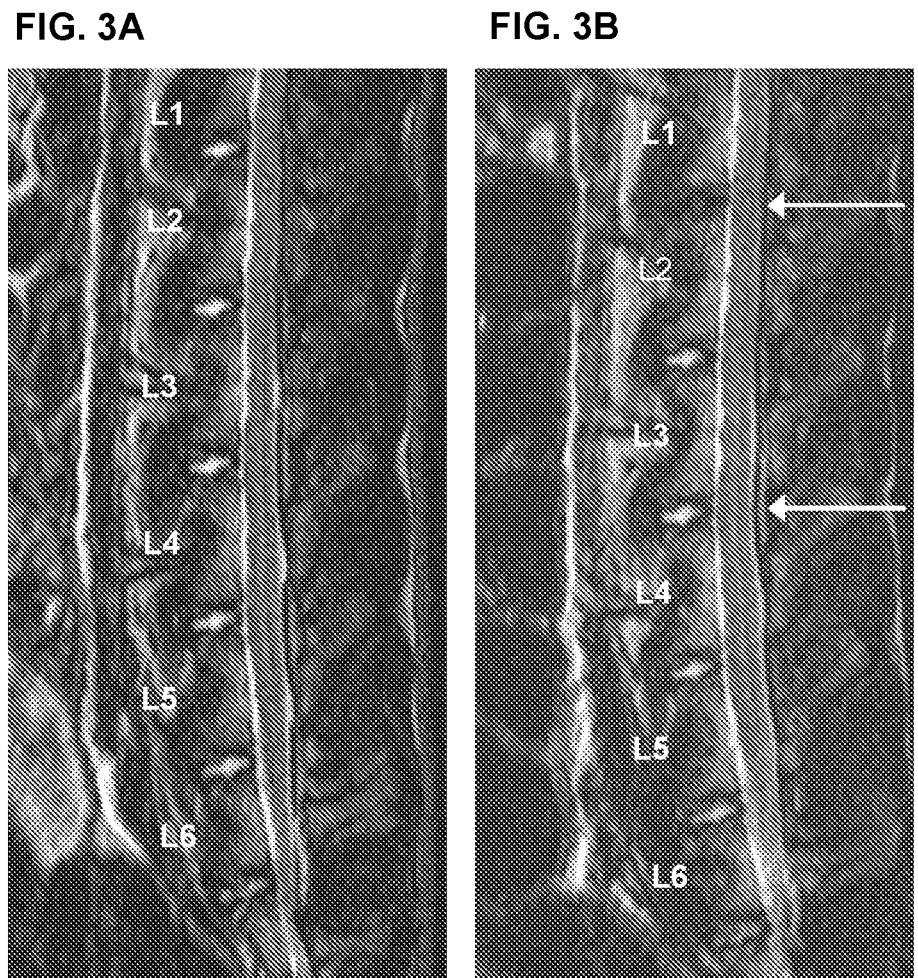
FIGS. 3A-3D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc. Mixed cell treatment in particular, has an intervertebral anti-degenerating effect.
Figures 3C, 3D:
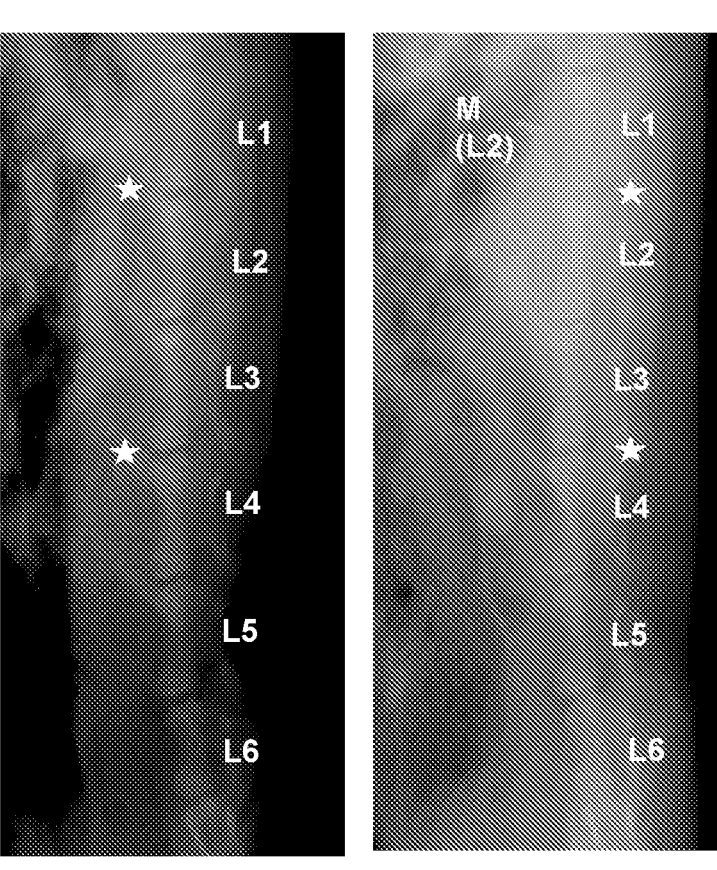
Figures 4C, 4D:
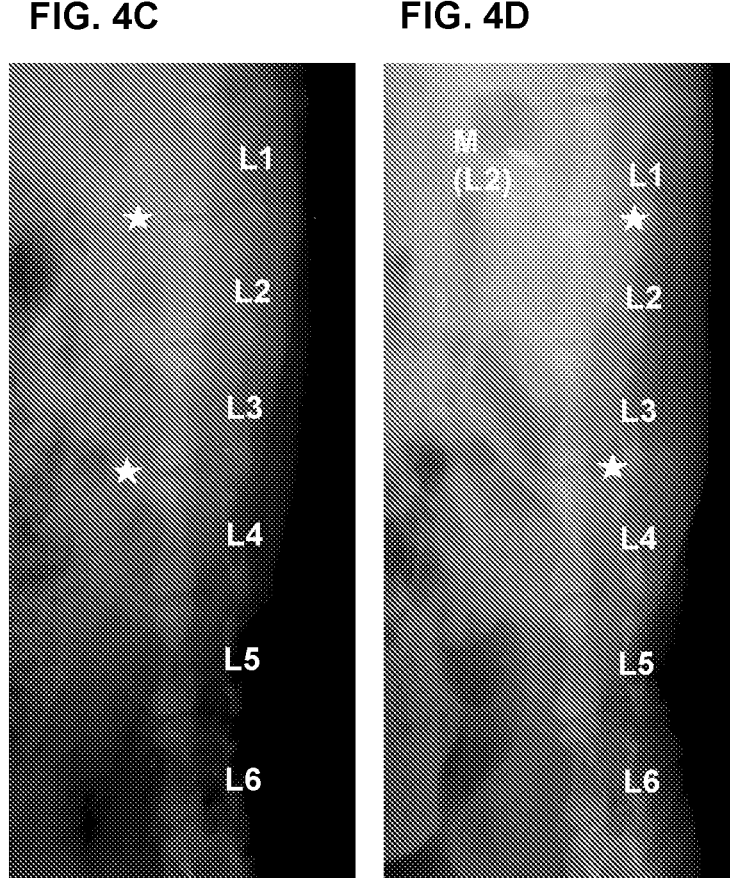
Figures 5A, 5B:
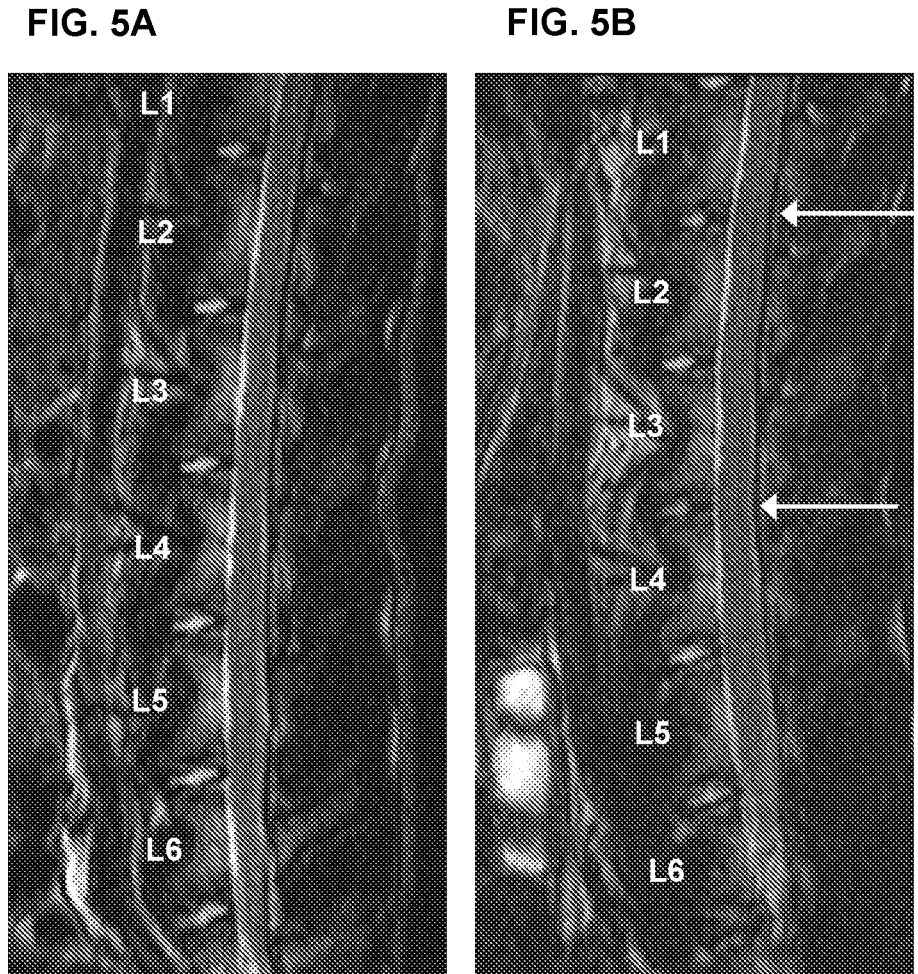

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "mammalian cells" in reference to transfected or transduced cells includes all types of mammalian cells, in particular human cells, including but not limited to connective tissue cells such as fibroblasts or chondrocytes, or stem cells, and in particular human embryonic kidney cells, and further in particular, human embryonic kidney 293 cells, or epithelial cells.

As used herein, the term "connective tissue" is any tissue that connects and supports other tissues or organs, and includes but is not limited to a ligament, a cartilage, a tendon, a bone, and a synovium of a mammalian host.

As used herein, the term "connective tissue cell" or "cell of a connective tissue" include cells that are found in the connective tissue, such as fibroblasts, cartilage cells (chondrocytes), and bone cells (osteoblasts/osteocytes), which secrete collagenous extracellular matrix, as well as fat cells (adipocytes) and smooth muscle cells. Preferably, the connective tissue cells are fibroblasts, chondrocytes, or bone cells. More preferably, the connective tissue cells are chondrocytes cells. It will be recognized that the invention can be practiced with a mixed culture of connective tissue cells, as well as cells of a single type. Preferably, the connective tissue cell does not cause a negative immune response when injected into the host organism. It is understood that allogeneic cells may be used in this regard, as well as autologous cells for cell-mediated gene therapy or somatic cell therapy.

As used herein, "connective tissue cell line" includes a plurality of connective tissue cells originating from a common parent cell.

As used herein, "hyaline cartilage" refers to the connective tissue covering the joint surface. By way of example only, hyaline cartilage includes, but is not limited to, articular cartilage, costal cartilage, and nose cartilage.

In particular, hyaline cartilage is known to be self-renewing, responds to alterations, and provides stable movement with less friction. Hyaline cartilage found even within the same joint or among joints varies in thickness, cell density, matrix composition and mechanical properties, yet retains the same general structure and function. Some of the functions of hyaline cartilage include surprising stiffness to compression, resilience, and exceptional ability to distribute weight loads, ability to minimize peak stress on subchondral bone, and great durability.

Grossly and histologically, hyaline cartilage appears as a slick, firm surface that resists deformation. The extracellular matrix of the cartilage comprises chondrocytes, but lacks blood vessels, lymphatic vessels or nerves. An elaborate, highly ordered structure that maintains interaction between chondrocytes and the matrix serves to maintain the structure and function of the hyaline cartilage, while maintaining a low level of metabolic activity. The reference O'Driscoll, J. Bone Joint Surg., 80A: 1795-1812, 1998 describes the structure and function of hyaline cartilage in detail, which is incorporated herein by reference in its entirety.

As used herein, "injectable" composition refers to a composition that excludes various three-dimensional scaffold, framework, mesh or felt structure, which may be made of any material or shape that allows cells to attach to it and allows cells to grow in more than one layer, and which structure is generally implanted, and not injected. In one embodiment, the injection method of the invention is typically carried out by a syringe. However, any mode of injecting the composition of interest may be used. For instance, catheters, sprayers, or temperature dependent polymer gels also may be used.

As used herein, "juvenile chondrocyte" refers to chondrocyte obtained from a human being who is less than two years old. Typically, the chondrocyte is obtained from preferably the hyaline cartilage region of an extremity of the body, such as a finger, nose, ear lobe and so forth. Juvenile chondrocytes may be used as donor chondrocytes for allogeneic treatment of defected or injured intervertebral disc.

As used herein, the term "mammalian host" includes members of the animal kingdom including but not limited to human beings.

As used herein, "mixed cell" or a "mixture of cells" or "cell mixture" refers to the combination of a plurality of cells that include a first population of cells that are transfected or transduced with a gene of interest and a second population of cells that are untransduced.

In one embodiment of the invention, mixed cells may refer to the combination of a plurality of cells that include cells that have been transfected or transduced with a gene or DNA encoding a member of the transforming growth factor β superfamily and cells that have not been transfected or transduced with a gene encoding a member of the transforming growth factor β superfamily Typically, the ratio of cells that have not been transfected or transduced with a gene encoding a member of the transforming growth factor β superfamily to cells that have been transfected or transduced with a TGF superfamily gene may be in the range of about 3-20 to 1. The range may include about 3-10 to 1. In particular, the range may be about 10 to 1 in terms of the number of cells. However, it is understood that the ratio of these cells should not be necessarily fixed to any particular range so long as the combination of these cells is effective to treat injured intervertebral disc by slowing or retarding degeneration of defected intervertebral disc.

As used herein, "non-disc chondrocyte" refers to chondrocytes isolated from any part of the body except for intervertebral disc cartilage tissue. Non-disc chondrocytes of the present invention may be used for allogeneic transplantation or injection into a patient to treat defected or injured intervertebral disc.

As used herein, the term "patient" includes members of the animal kingdom including but not limited to human beings.

As used herein, the term "primed" cell refers to cells that have been activated or changed to express certain genes.

As used herein, "slowing" or "prevention" of intervertebral disc degeneration refers to the retention of volume of intervertebral disc or height of the disc over time compared with the volume or height level that would normally be found at the site of injury leading to normal degeneration over a given time. This may mean a percentage increase of volume or height, such as about 10%, 20%, 30%, 40%, 50%, 60%, 70%, 80%, or 90% compared with the normal expected degeneration levels at a given time, or may mean lessening of damage or depletion of volume or height of the intervertebral disc at the locus.

As used herein, the "transforming growth factor-$\beta$ (TGF-$\beta$) superfamily" encompasses a group of structurally related proteins, which affect a wide range of differentiation processes during embryonic development. The family includes, Müllerian inhibiting substance (MIS), which is required for normal male sex development (Behringer, et al., Nature, 345:167, 1990), *Drosophila* decapentaplegic (DPP) gene product, which is required for dorsal-ventral axis formation and morphogenesis of the imaginal discs (Padgett, et al., Nature, 325:81-84, 1987), the *Xenopus* Vg-1 gene product, which localizes to the vegetal pole of eggs (Weeks, et al., Cell, 51:861-867, 1987), the activins (Mason, et al., Biochem, Biophys. Res. Commun., 135:957-964, 1986), which can induce the formation of mesoderm and anterior structures in *Xenopus* embryos (Thomsen, et al., Cell, 63:485, 1990), and the bone morphogenetic proteins (BMP's, such as BMP-2, 3, 4, 5, 6 and 7, osteogenin, OP-1) which can induce de novo cartilage and bone formation (Sampath, et al., J. Biol. Chem., 265:13198, 1990). The TGF-$\beta$ gene products can influence a variety of differentiation processes, including adipogenesis, myogenesis, chondrogenesis, hematopoiesis, and epithelial cell differentiation (for a review, see Massague, Cell 49:437, 1987), which is incorporated herein by reference in its entirety.

The proteins of the TGF-$\beta$ family are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-$\beta$'s (Cheifetz, et al., Cell, 48:409, 1987), heterodimers have also been detected, and these appear to have different biological properties than the respective homodimers.

Members of the superfamily of TGF-$\beta$ genes include TGF-$\beta$3, TGF-$\beta$2, TGF-$\beta$4 (chicken), TGF-$\beta$1, TGF-$\beta$5 (*Xenopus*), BMP-2, BMP-4, *Drosophila* DPP, BMP-5, BMP-6, Vgr1, OP-1/BMP-7, *Drosophila* 60A, GDF-1, *Xenopus* Vgf, BMP-3, Inhibin-$\beta$A, Inhibin-13B, Inhibin-$\alpha$, and MIS. These genes are discussed in Massague, Ann. Rev. Biochem. 67:753-791, 1998, which is incorporated herein by reference in its entirety.

Preferably, the member of the superfamily of TGF-$\beta$ genes is TGF-$\beta$1, TGF-$\beta$2, TGF-$\beta$3, BMP-2, BMP-3, BMP-4, BMP-5, BMP-6, or BMP-7.

Intervertebral Disc

The intervertebral discs make up one fourth of the spinal column's length. There are no discs between the Atlas (C1), Axis (C2), and Coccyx. Discs are not vascular and therefore depend on the end plates to diffuse needed nutrients. The cartilaginous layers of the end plates anchor the discs in place.

The intervertebral discs are fibrocartilaginous cushions serving as the spine's shock absorbing system, which protect the vertebrae, brain, and other structures (i.e. nerves). The discs allow some vertebral motion: extension and flexion. Individual disc movement is very limited—however considerable motion is possible when several discs combine forces.

Intervertebral discs are composed of an annulus fibrosus and a nucleus pulposus. The annulus fibrosus is a strong radial tire-like structure made up of lamellae; concentric sheets of collagen fibers connected to the vertebral end plates. The sheets are orientated at various angles. The annulus fibrosus encloses the nucleus pulposus.

Although both the annulus fibrosus and nucleus pulposus are composed of water, collagen, and proteoglycans (PGs), the amount of fluid (water and PGs) is greatest in the nucleus pulposus. PG molecules are important because they attract and retain water. The nucleus pulposus contains a hydrated gel-like matter that resists compression. The amount of water in the nucleus varies throughout the day depending on activity. As people age, the nucleus pulposus begins to dehydrate, which limits its ability to absorb shock. The annulus fibrosus gets weaker with age and begins to tear. While this may not cause pain in some people, in others one or both of these may cause chronic pain.

Pain due to the inability of the dehydrating nucleus pulposus to absorb shock is called axial pain or disc space pain. One generally refers to the gradual dehydration of the nucleus pulposus as degenerative disc disease. When the annulus fibrosus tears due to an injury or the aging process, the nucleus pulposus can begin to extrude through the tear. This is called disc herniation. Near the posterior side of each disc, all along the spine, major spinal nerves extend out to different organs, tissues, extremities etc. It is very common for the herniated disc to press against these nerves (pinched nerve) causing radiating pain, numbness, tingling, and diminished strength and/or range of motion. In addition, the contact of the inner nuclear gel, which contains inflammatory proteins, with a nerve can also cause significant pain. Nerve-related pain is called radicular pain.

Herniated discs go by many names and these can mean different things to different medical professionals. A slipped disc, ruptured disc, or a bulging disc can all refer to the same medical condition. Protrusions of the disc into the adjacent vertebra are known as Schmorl's nodes.

Primed Cell Therapy

The present invention encompasses administering primed cells to an intervertebral disc region in a mammal to treat injured intervertebral disc by preventing or retarding degeneration of intervertebral disc. Primed cells are typically connective tissue cells, and include chondrocytes or fibroblasts.

By way of example, when a population of primary chondrocytes are passaged about 3 or 4 times, their morphology typically changes to fibroblastic chondrocytes. As primary chondrocytes are passaged, they begin to lose some of their chondrocytic characteristics and begin to take on the characteristics of fibroblastic chondrocytes. When these fibroblastic chondrocytes are incubated or "primed" with a cytokine such as a protein from the TGF-β superfamily, the cells regain their chondrocytic characteristics, which include production of collagen.

Such primed cells include fibroblastic chondrocytes, which have been incubated with TGFβ1, and as a result have reverted to collagen producing chondrocytes. An advantage of using primed cells in retardation of intervertebral disc degeneration is the ease of creating useable chondrocytes for introduction into the intervertebral disc for production of collagen and otherwise maintenance of the cartilaginous matrix.

The cells may include without limitation primary cells or cells which have undergone about one to twenty passages. The cells may be connective tissue cells. The cells may include cells that have undergone a morphogenic change, wherein the priming causes reversion to the characteristics of the original cell. The cells may include without limitation chondrocytes, fibroblasts, or fibroblastic chondrocytes. Priming may occur by incubating the cells for a period of at least 40 hours, or from 1 to 40 hours, from 2 to 30 hours, from 3 to 25 hours, from 4 to 20 hours, from 5 to 20, from 6 to 18 hours, 7 to 17 hours, 8 to 15 hours, or 9 to 14 hours, with a cytokine, and then optionally separating the cytokine from the cells and injecting the primed cells into a cartilaginous defect site of interest in order to regenerate cartilage, preferably hyaline cartilage. In one aspect, the cytokine may be a member of the superfamily of TGF-β. In particular, the cytokine may be TGF-β, and in particular, TGF-β1.

The cytokine may be present in the priming incubation mix in an amount to sufficiently "prime" the chondrocyte to be useful in the intervertebral treatment method. In this aspect, the priming incubation mix may contain at least about 1 ng/ml of the cytokine. In particular, the mix may contain from about 1 to 1000 ng/ml, from about 1 to 750 ng/ml, from about 1 to 500 ng/ml, from about 1 to 400 ng/ml, from about 1 to 300 ng/ml, from about 1 to 250 ng/ml, from about 1 to 200 ng/ml, from about 1 to 150 ng/ml, from about 1 to 100 ng/ml, from about 1 to 75 ng/ml, from about 1 to 50 ng/ml, from about 10 to 500 ng/ml, from about 10 to 400 ng/ml, from about 10 to 300 ng/ml, from about 10 to 250 ng/ml, from about 10 to 200 ng/ml, from about 10 to 150 ng/ml, from about 10 to 100 ng/ml, from about 10 to 75 ng/ml, from about 10 to 50 ng/ml, from about 15 to 500 ng/ml, from about 15 to 400 ng/ml, from about 15 to 300 ng/ml, from about 15 to 250 ng/ml, from about 15 to 200 ng/ml, from about 15 to 150 ng/ml, from about 15 to 100 ng/ml, from about 15 to 75 ng/ml, from about 15 to 50 ng/ml, from about 20 to 500 ng/ml, from about 20 to 400 ng/ml, from about 20 to 300 ng/ml, from about 20 to 250 ng/ml, from about 20 to 200 ng/ml, from about 20 to 150 ng/ml, from about 20 to 100 ng/ml, from about 20 to 75 ng/ml, from about 20 to 50 ng/ml, from about 25 to 500 ng/ml, from about 25 to 400 ng/ml, from about 25 to 300 ng/ml, from about 25 to 250 ng/ml, from about 25 to 200 ng/ml, from about 25 to 150 ng/ml, from about 25 to 100 ng/ml, from about 25 to 75 ng/ml, from about 25 to 50 ng/ml, from about 30 to 500 ng/ml, from about 30 to 400 ng/ml, from about 30 to 300 ng/ml, from about 30 to 250 ng/ml, from about 30 to 200 ng/ml, from about 30 to 150 ng/ml, from about 30 to 100 ng/ml, from about 30 to 75 ng/ml, from about 30 to 50 ng/ml, from about 35 to 500 ng/ml, from about 35 to 400 ng/ml, from about 35 to 300 ng/ml, from about 35 to 250 ng/ml, from about 35 to 200 ng/ml, from about 35 to 150 ng/ml, from about 35 to 100 ng/ml, from about 35 to 75 ng/ml, from about 35 to 50 ng/ml, from about 40 to 500 ng/ml, from about 40 to 400 ng/ml, from about 40 to 300 ng/ml, from about 40 to 250 ng/ml, from about 40 to 200 ng/ml, from about 40 to 150 ng/ml, from about 40 to 100 ng/ml, from about 40 to 75 ng/ml, or from about 40 to 50 ng/ml.

One method of practicing the invention may include incubating the cells with a cytokine for a certain length of time to create primed cells and optionally separating the cytokine from the cells, and injecting the primed cells into intervertebral disc or the site of interest near it. Alternatively, the cells may be incubated with the cytokine of interest for a time and the combination may be administered to the site of defect without separating out the cytokine.

It is to be understood that while it is possible that substances such as a scaffolding or a framework as well as various extraneous tissues may be implanted together in the primed cell therapy protocol of the present invention, it is also possible that such scaffolding or tissue not be included in the injection system of the invention. In a preferred embodiment, in the inventive somatic cell therapy, the invention is directed to a simple method of injecting a population of primed connective tissue cells to the intervertebral disc space.

It will be understood by the artisan of ordinary skill that the source of cells for treating a human patient may be the patient's own cells, but that allogeneic cells as well as xenogeneic cells may also be used without regard to the histocompatibility of the cells. Alternatively, in one embodiment of the invention, allogeneic cells may be used having matching histocompatibility to the mammalian host. To describe in further detail, the histocompatibility of the donor and the patient are determined so that histocompatible cells are administered to the mammalian host. Also, juvenile chondrocytes may also be used allogeneically without necessarily determining the histocompatibility of the donor and the patient.

Gene Delivery

In one aspect the present invention discloses ex vivo and in vivo techniques for delivery of a DNA sequence of interest to the connective tissue cells of the mammalian host. The ex vivo technique involves culture of target mammalian cells, in vitro transfection of the DNA sequence, DNA vector or other delivery vehicle of interest into the mammalian cells, followed by transplantation of the modified mammalian cells to the target area of the mammalian host, so as to effect in vivo expression of the gene product of interest.

It is to be understood that while it is possible that substances such as a scaffolding or a framework as well as various extraneous tissues may be implanted together in the protocol of the present invention, it is preferred that such scaffolding or tissue not be included in the injection system of the invention. In a one embodiment, the invention is directed to a simple method of injecting a TGF superfamily protein or a population of cultured, untransfected/untransduced connective tissue cells or transfected/transduced mammalian cells or a mixture thereof to the intervertebral disc space so that the exogenous TGF superfamily protein is expressed or is active in the space.

It will be understood by the artisan of ordinary skill that one source of cells for treating a human patient is the patient's own cells. Another source of cells includes allogeneic cells without regard to the histocompatibility of the cells to the patient sought to be treated.

More specifically, this method includes employing a gene product that is a member of the transforming growth factor β superfamily, or a biologically active derivative or fragment thereof, or a biologically active derivative or fragment thereof.

In another embodiment of this invention, a compound for parenteral administration to a patient in a therapeutically effective amount is provided that contains a TGF-β superfamily protein and a suitable pharmaceutical carrier.

Another embodiment of this invention provides for a compound for parenteral administration to a patient in a prophylactically effective amount that includes a TGF-β superfamily protein and a suitable pharmaceutical carrier.

In therapeutic applications, the TGF-β protein may be formulated for localized administration. Techniques and formulations generally may be found in Remington's Pharmaceutical Sciences, Mack Publishing Co., Easton, Pa., latest edition. The active ingredient that is the TGF protein is generally combined with a carrier such as a diluent of excipient which may include fillers, extenders, binding, wetting agents, disintegrants, surface-active agents, erodable polymers or lubricants, depending on the nature of the mode of administration and dosage forms. Typical dosage forms include, powders, liquid preparations including suspensions, emulsions and solutions, granules, and capsules.

The TGF protein of the present invention may also be combined with a pharmaceutically acceptable carrier for administration to a subject. Examples of suitable pharmaceutical carriers are a variety of cationic lipids, including, but not limited to N-(1-2,3-dioleyloxy)propyl)-n,n,n-trimethylammonium chloride (DOTMA) and dioleoylphophotidyl ethanolamine (DOPE). Liposomes are also suitable carriers for the TGF protein molecules of the invention. Another suitable carrier is a slow-release gel or polymer comprising the TGF protein molecules.

The TGF beta protein may be mixed with an amount of a physiologically acceptable carrier or diluent, such as a saline solution or other suitable liquid. The TGF protein molecule may also be combined with other carrier means to protect the TGF protein and biologically active forms thereof from degradation until they reach their targets and/or facilitate movement of the TGF protein or biologically active form thereof across tissue barriers.

A further embodiment of this invention includes storing the cell prior to transferring the cells. It will be appreciated by those skilled in the art that the cells may be stored frozen in 10 percent DMSO in liquid nitrogen.

In the present application, a method is provided for regenerating or preventing degeneration of intervertebral disc by injecting an appropriate mammalian cell that is transfected or transduced with a gene encoding a member of the transforming growth factor-beta (TGF-β) superfamily, including, but not limited to, BMP-2 and TGF-β 1, 2, and 3.

In another embodiment of the present application, a method is provided for preventing or retarding degeneration of intervertebral disc by injecting an appropriate connective tissue cell that is not transfected or transduced with a gene encoding a member of the transforming growth factor-beta (TGF-β) superfamily or that is not transfected or transduced with any other gene. In another aspect, the invention is directed to treating injured or degenerated intervertebral disc by preventing or retarding degeneration of the intervertebral disc by using the above-described method.

In another embodiment of the present application, a method is provided for preventing or retarding degeneration of intervertebral disc by injecting an appropriate mammalian cell that is transfected or transduced with a gene encoding a member of the transforming growth factor-beta (TGF-β) superfamily. In another aspect, the invention is directed to treating injured or degenerated intervertebral disc by preventing or retarding degeneration of the intervertebral disc by using the above-described method.

In another embodiment of the invention, a method is provided for preventing or retarding degeneration of intervertebral disc by injecting a combination of or a mixture of an appropriate mammalian cell that is transfected or transduced with a gene encoding a member of the transforming growth factor-beta (TGF-β) superfamily and an appropriate connective tissue cell that is not transfected or transduced with a gene encoding a member of the transforming growth factor-beta (TGF-β) superfamily or that is not transfected or transduced with any other gene. In another aspect, the invention is directed to treating injured or degenerated intervertebral disc by preventing or retarding degeneration of the intervertebral disc by using the above-described method.

In an embodiment of the invention, it is understood that the cells may be injected into the area in which degeneration of the intervertebral disc is to be sought to be prevented or retarded by using the cell above-described composition with or without scaffolding material or any other auxiliary material, such as extraneous cells or other biocompatible carriers. That is, the modified cells alone, unmodified cells alone, or a mixture or combination thereof may be injected into the area in which the degeneration of the intervertebral disc is sought to be prevented or retarded.

The following examples are offered by way of illustration of the present invention, and not by way of limitation.

EXAMPLES

Example I—Materials and Methods

Plasmid Construction

The plasmid pMTMLVβ1 was generated by subcloning a 1.2-kb Bgl II fragment containing the TGF-β1 coding sequence and a growth hormone poly A site at the 3' end into the Bam HI site of pMTMLV. pMTMLV vector was derived from the retroviral vector MFG by deleting entire gag and env sequences as well as some of ψ packaging sequence.

Cell Culture and Transduction—

The TGF-β cDNA cloned in retroviral vectors were individually transduced into 293 cells (293-TGF-β1). They were cultured in Dulbecco's Modified Eagle's Medium (GIBCO-BRL, Rockville, Md.) with 10% concentration of fetal bovine serum.

To select the cells with the transduced gene sequence, neomycin (300 μg/ml) was added into the medium. The cells with TGF-β1 expression were sometimes stored in liquid nitrogen and cultured just before the injection.

Radiographic Analysis of Disc Height

Radiographs were taken after administration of ketamine hydrochloride (25 mg/kg) and Rompun (1 mg/kg) at various week intervals after the puncture. Extreme care was taken to maintain a consistent level of anesthesia during radiography of each animal and at each time to obtain a similar degree of muscle relaxation, which may affect the disc height. Therefore, the preoperative radiograph was always used as a baseline measurement. Efforts were also made to keep the spine in a slightly flexed position. To decrease the error from axial rotation of the spine and beam divergence, radiographs were repeated at least twice on each animal in the lateral decubitus position, with the beam centered at 4 cm from the rabbit iliac crest. Radiographs were digitally scanned and digitally stored using an Image Capture software.

Image Analysis

Using digitized radiographs, measurements, including the vertebral body height and IVD height, were analyzed using the public domain image analysis. The data were transported to Excel software, and the IVD height was expressed as the DHI using the method of Lu et al. "Effects of chondroitinase ABC and chymopapain on spinal motion segment biomechanics. An in vivo biomechanical, radiologic, and histologic canine study", Spine 1997; 22:1828-34. Average IVD height (DHI) was calculated by averaging the measurements obtained from the anterior, middle, and posterior portions of the IVD and dividing that by the average of adjacent vertebral body heights. Changes in the DHI of injected discs were expressed as percent DHI and normalized to the measured preoperative IVD height (percent DHI=postoperative DHI/preoperative DHI×100). The within-subject standard deviation (Sw) was calculated using the equation:

$$\sqrt{(\Sigma x_1 - x_2)^2 / 2n}$$

Where $X_1$ is the first measurement value, $X_2$ is the second measurement value, and n=450. The percent coefficient of variance (percent CV) was calculated as (Sw/means of all measurements×100). The intraobserver error of DHI measurements was estimated to be minimal (Sw: 0.001800316; percent CV: 3.13). The interobserver error was also reported to be small (Sw: 0.003227; percent CV: 9.6)

MRI Assessments

MRI examinations were performed on all rabbits in the study using a 0.3-T imager (Airis II, version 4.0 A; Hitachi Medical System America, Inc.) with a quadrature extremity coil receiver. After sacrifice, the spinal columns with surrounding soft tissue were isolated and subjected to MRI analysis. T2-weighted sections in the sagittal plane were obtained in the following settings: fast spin echo sequence with TR (time to repetition) of 4000 milliseconds and TE (time to echo) of 120 milliseconds; 256(h)×128 (v) matrix; field of view of 260; and 4 excitations. The section thickness was 2 mm with a 0-mm gap. A blinded observer using the modified Thompson classification based on changes in the degree and area of signal intensity from grade 1 to 4 (1=normal, 2=minimal decrease of signal intensity but obvious narrowing of high signal area, 3=moderate decrease of signal intensity, and 4=severe decrease of signal intensity) evaluated MRIs. The intraobserver and interobserver reliability correlation coefficients of MRI grading based on 2 evaluations were excellent (K=0.98, 0.90, respectively), as determined by the Cohen kappa correlation coefficient.

Example II—Experimental Methods and Results

Preventing Degeneration of Injured Intervertebral Disc

New Zealand white male rabbits were used. An open surgical technique was used. Three intervertebral levels in the lumbar spine: L2-3, L3-4, L4-5 were experimentally treated or observed as a control in each animal. Treatments were assigned to levels in a balanced manner with multiple sites/discs per rabbit observed. Within subject design, pre-post surgery comparisons, change across disc levels were used as controls.

Example III

Preventing Degeneration of Injured Intervertebral Disc Using Untransduced Chondrocyte Alone, TGF-β1-Producing 293 Cells Alone, or with Mixed-Cells (Human Chondrocytes and TGF-β1-Producing 293 Cells) Injection in Rabbits All of the chondrocytes used in Examples I-V are non-disc chondrocytes and are juvenile chondrocytes, obtained from the hyaline cartilage portion of a finger of a less than two year old child.

Needle puncture was produced in the intervertebral discs of the lumbar spine.

After this needle puncture, TGF-β1-producing 293 cells, primary untransduced human chondrocytes, mixture of TGF-β1-producing 293 cells and primary untransduced human chondrocytes, primed untransduced human chondrocytes or carrier/media are injected. Several controls are used. Experimental conditions are listed below Table I.

TABLE I

| Surgical Preparation | Injection Treatment |
|---|---|
| Needle puncture | TGF-β1-producing 293 cells (~5 × 10⁶cells) |
| Needle Puncture | Mixed: TGF-β1-producing 293 cells Primary untransduced human chondrocytes (~3 to 1 ratio, 5 × 10⁶) |
| Needle Puncture | Primary untransduced human chondrocytes (~5 × 10⁶) |
| Needle Puncture | Primed untransduced human chondrocytes (~5 × 10⁶) |
| Needle puncture | DMEM |
| Needle puncture | Needle puncture only-no injection |
| No puncture | No puncture no treatment control |

Briefly, a needle puncture injury is produced in the intervertebral discs of the lumbar spine of rabbit or a pig. After this needle puncture, rabbits are left to heal for 4 weeks. Then in a second surgical procedure, experimental treatment composition, which includes TGF-β1-producing 293 cells and/or primary untransduced human chondrocytes ($\sim$5×10$^5$) is injected or control conditions observed (Table I).

After endotrachial intubation and general anesthesia is achieved such as by administration of ketamine hydrochloride and Rompun®, the animal is placed in supine position. Lactated ringers are used at about (5 ml/kg/hr). The area of incision is shaved and prepped and draped in the usual sterile fashion with alternating betadine scrubs and alcohol wipes (>three times). Bland ophthalmic ointment is placed on the eyes. A left retroperitoneal approach is used to expose the right anterior aspect of the disc from L2-L5 (the rabbit has 6 to 7 lumbar vertebra). Various preparation schemes are used and treatment schema is applied to each disc level. For 'Needle Puncture' preparation of the disc, a 18-gauge needle is used to place a puncture in the disc at the depth of 5 mm (Aoki et al., "Nerve fiber ingrowth into scar tissue formed following nucleus pulposus extrusion in the rabbit annular-puncture disc degeneration model: effects of depth of puncture." Spine. 2006; 31(21):E774-80). After puncture, the test materials listed in Table I are injected. Treatment composition is applied to any one of L1-2, L2-3, L3-4, L4-5 region of each rabbit.

Monthly radiographs are used to monitor any disc changes. Animals are sacrificed at 2, 8, and 24 weeks after surgery.

Radiographs/MRI.

Healing is indicated by a detectable radiographic change of increased disc height from same disc at baseline (pre op) compared to disc at other disc levels. Other discs are compared before and after needle puncture only, and disc before and after no needle puncture yielding an index of normal degeneration over time.

Retro-Transcription PCR.

Retro-transcription PCR is performed to assay relative quantity of surviving transfected chrondrocytes.

Histology.

Also histology is used to confirm characterization of the collagen type I and type II and the gross appearance and evaluation of de novo chondrocytes.

Western Blot analysis and or ELISA.

Quantatitive expression of collagen type I and type II, and proteoglycan concentration, Smads 2/3, Sox-9. Additionally ELISA is used to evaluate TGFβ-1, BMP2, BMP7, GDF5 and other related growth factors where there are available antibodies.

Apoptosis is examined in the other tissue structures of the intervertebral disc via observing the expression of Capase-3.

Example IV

Results

The results are as shown in the Figures and the description of the Figures of the present application. Punctured intervertebral disc treated with untransduced chondrocytes alone, transduced 293 cells alone, primed chondrocyte alone or a mixture of transduced 293 cells and untransduced chondrocytes, show beneficial effects in preventing or retarding disc degeneration compared with vehicle control.

Example IV-1—Mixed-Cell (Transduced 293 Cells and Untransduced Chondrocytes) Treatment of Punctured Intervertebral Disc in Rabbit Mixed cell treatment has an intervertebral anti-degenerating effects when tested on rabbits. The effect is seen in a variety of experiments in FIGS. 1-4. FIGS. 1A-1F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment is seen at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows MRI radiograph of a rabbit spine eight (8) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc.

FIGS. 2A-2F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows MRI radiograph of a rabbit spine eight (8) weeks after surgery in which (i) the disc at L1/2 was injured and TGF-β1-producing 293 cells were injected, (ii) no puncture and no treatment is seen at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc.

FIGS. 3A-3D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and TGF-β1-producing 293 cells were injected, (ii) no puncture and no treatment control at spine locus L2/3, and (iii) disc at L3/4 was injured and mixture of TGF-β1-producing 293 cells and untransduced human chondrocytes in 1:3 ratio were injected; arrows point to L1/2 and L3/4 disc region. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc.

Example IV-2—Transduced 293 Cell Treatment of Punctured Intervertebral Disc in Rabbit TGF-β1-producing 293 cells treatment has an intervertebral anti-degenerating effect. The effect is seen in FIGS. 4A-4D, which show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and mixture of TGF-β1-producing 293 cells and untransduced human chondrocytes in 1:3 ratio were injected, (ii) no puncture and no treatment control at spine locus L2/3, and (iii) disc at L3/4 was injured and TGF-β1-producing 293 cells were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc.

Example IV-3—Transduced 293 Cell Treatment and Mixed-Cell Treatment of Punctured Intervertebral Disc in Rabbit TGF-β1-producing 293 cell treatment and mixed cell treatments have an intervertebral anti-degenerating effect. The effect is seen in FIGS. 5A-5D, which show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and mixture of TGF-β1-producing 293 cells and untransduced human chondrocytes in 1:3 ratio were injected, (ii) no puncture and no treatment control at spine locus L2/3, and (iii) disc at L3/4 was injured and TGF-β1-producing 293 cells were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc.

Figures 7A, 7B, 7C:
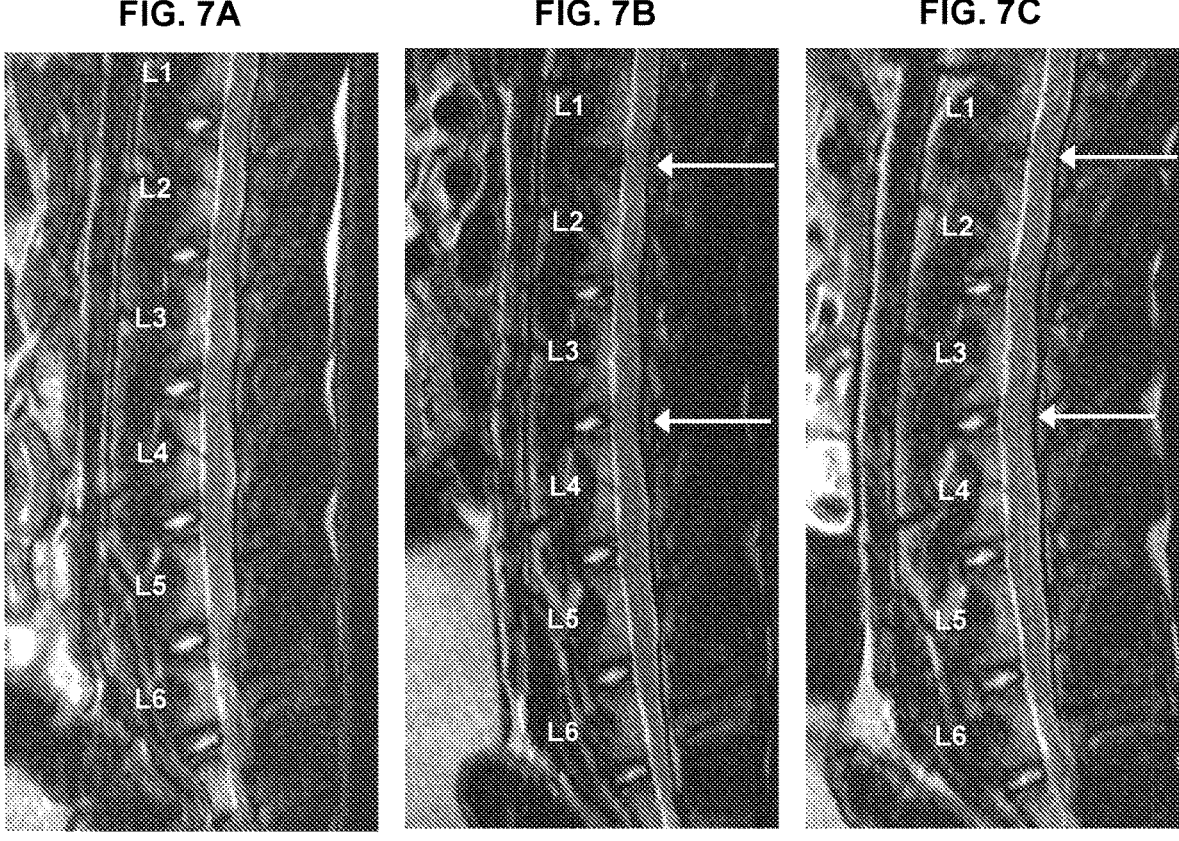
Figure 7D:
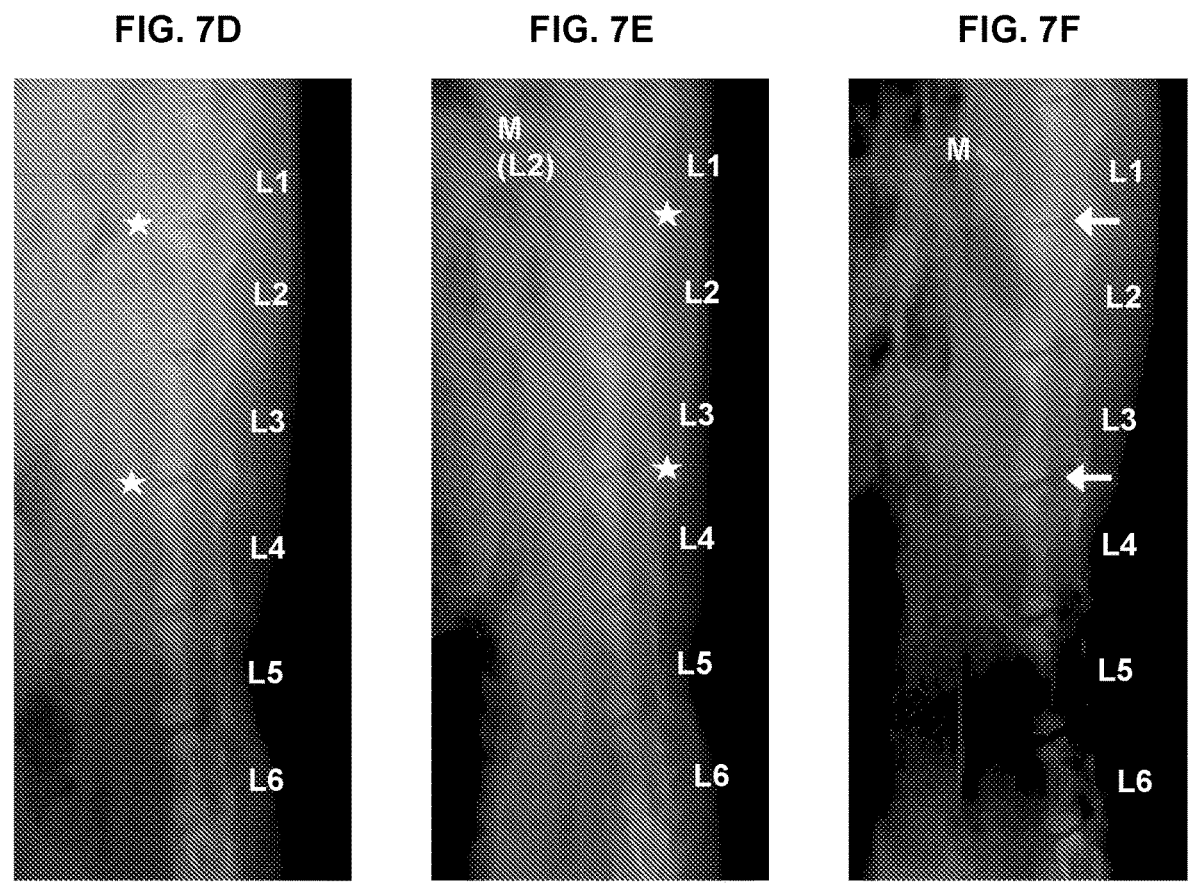
Figures 8A, 8B, 8C:
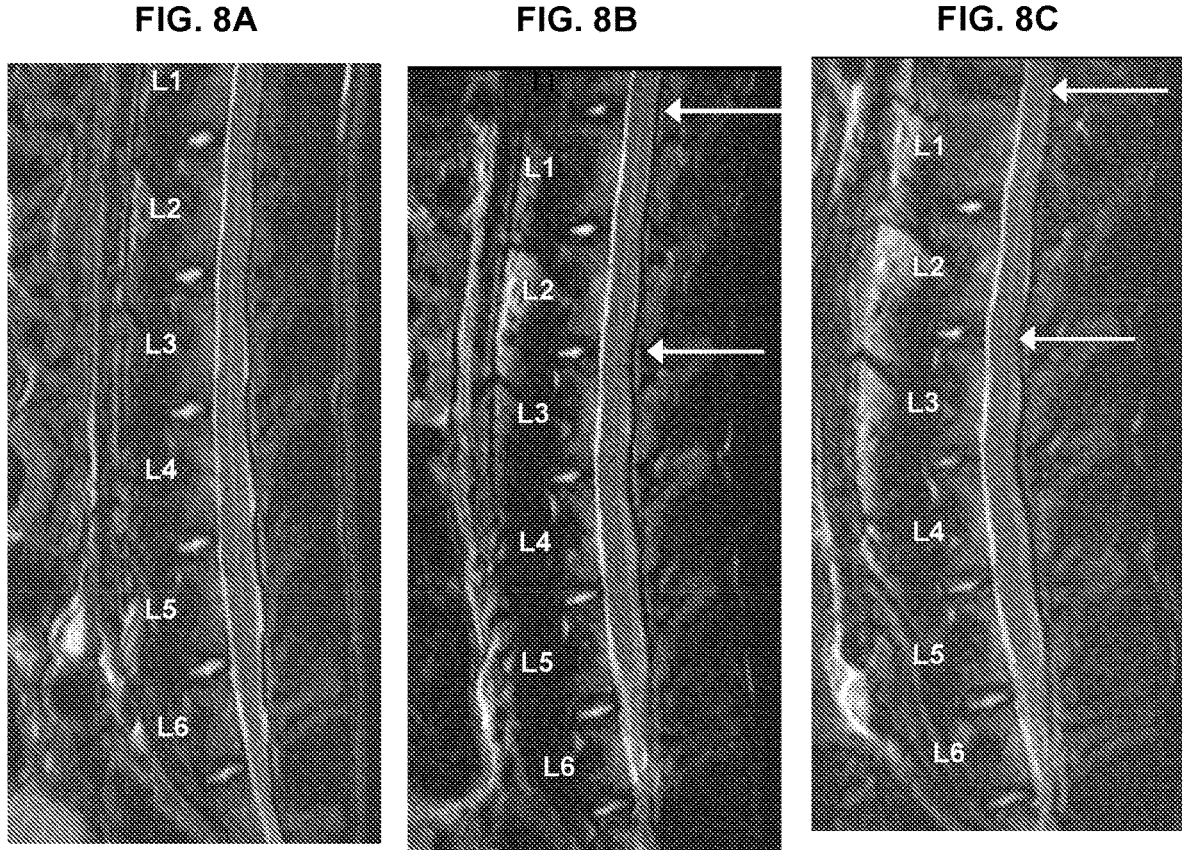
FIGS. 8A-8F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at T12/L1 was injured by needle puncture and no injection, (ii) no puncture and no treatment control at spine locus L1/2, and (iii) disc at L2/3 was injured and untransduced chondrocytes were injected; arrows point to T12/L1 and L2/3 disc regions. (C) shows MRI radiograph of a rabbit spine eight (8) weeks after surgery in which (i) the disc at T12/L1 was injured by needle puncture and no injection, (ii) no puncture and no treatment control at spine locus L1/2, and (iii) disc at L2/3 was injured and untransduced chondrocytes were injected; arrows point to T12/L1 and L2/3 disc regions. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc. Untransduced chondrocytes treatment has an intervertebral anti-degenerating effect.
Figures 8D, 8E, 8F:
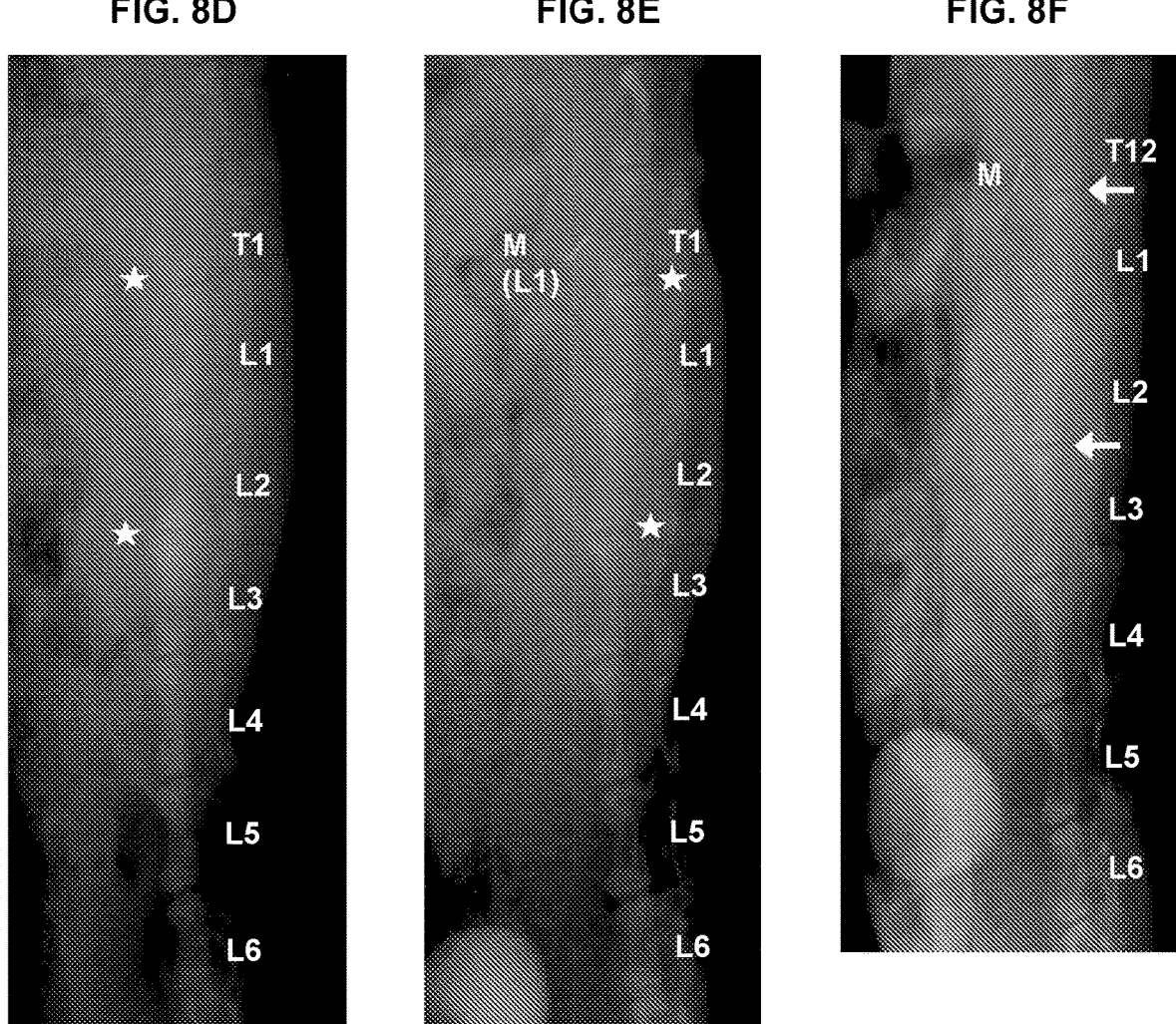

Example IV-4—Untransduced Chondrocyte Treatment of Punctured Intervertebral Disc in Rabbit Untransduced chondrocyte treatment has an intervertebral anti-degenerating effect. The effect is seen in a variety of experiments in FIGS. 6-8. FIGS. 6A-6D show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc.

FIGS. 7A-7F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (C) shows MRI radiograph of a rabbit spine eight (8) weeks after surgery in which (i) the disc at L1/2 was injured and cell culture media DMEM was injected, (ii) no puncture and no treatment control at spine locus L2/3, and (iii) disc at L3/4 was injured and untransduced chondrocytes were injected; arrows point to L1/2 and L3/4 disc regions. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc.

FIGS. 8A-8F show a slowing, retardation or prevention of degeneration of injured disc. (A) shows MRI radiograph of rabbit spine pre-surgery; (B) shows MRI radiograph of a rabbit spine four (4) weeks after surgery in which (i) the disc at T12/L1 was injured by needle puncture and no injection, (ii) no puncture and no treatment control at spine locus L1/2, and (iii) disc at L2/3 was injured and untransduced chondrocytes were injected; arrows point to T12/L1 and L2/3 disc regions. (C) shows MRI radiograph of a rabbit spine eight (8) weeks after surgery in which (i) the disc at T12/L1 was injured by needle puncture and no injection, (ii) no puncture and no treatment control at spine locus L1/2, and (iii) disc at L2/3 was injured and untransduced chondrocytes were injected; arrows point to T12/L1 and L2/3 disc regions. (D) shows X-ray radiograph of the rabbit described in (A) above, which is used to obtain a disc height index of the intervertebral disc to measure its morphology, its level of degeneration or regeneration. (E) shows X-ray radiograph of the rabbit described in (B) above, which is used to obtain a disc height index of the intervertebral disc. (F) shows X-ray radiograph of the rabbit described in (C) above, which is used to obtain a disc height index of the intervertebral disc.

Example IV-5—Untransduced Primed Chondrocyte Treatment of Punctured Intervertebral Disc in Rabbit Primed chondrocyte treatment has an intervertebral anti-degenerating effect. The effect is seen in FIGS. 9A-9D, which show a slowing, retardation or prevention of degeneration of injured disc. (A) shows MRI radiograph of rabbit spine pre-surgery; (B) shows MRI radiograph of a rabbit spine eight (8) weeks after surgery in which (i) the disc at L2/3 was injured and cell culture media DMEM was injected, (ii) no puncture and no treatment control at spine locus L3/4, and (iii) disc at L4/5 was injured and primed chondrocytes were injected; arrows point to L2/3 and L4/5 disc regions. (C) shows X-ray radiograph of the rabbit described in (A) above, which is used to obtain a disc height index of the intervertebral disc to measure its morphology, its level of degeneration or regeneration. (D) shows X-ray radiograph of the rabbit described in (B) above, which is used to obtain a disc height index of the intervertebral disc.

Example V

Source of Human Chondrocytes

Primary human chondrocytes were grown from cartilage tissue obtained from the surgical excision of a polydactyly finger from a one-year-old female human donor. The polydactyl tissue was harvested in a surgical room. The following procedure for chondrocyte isolation was performed in a biosafety cabinet. The plastic bottle containing the cartilage tissue was swiped with alcohol and the cartilage tissue was washed with sterile PBS (1×) using a pipette. A collagenase solution was prepared by dissolving 7 mg of collagenase (Gibco BRL) in 10 mL of DMEM (containing 10% FBS) and filtering through a 0.2 μm syringe filter (Corning). The washed cartilage tissue was treated with the collagenase solution for 17 to 18 hrs in a 37° C. shaker incubator. On the following day, the bottle was sanitized with alcohol. The collagenase treated material was pipetted up and down several times to separate loose cells from the tissue mass. After pipetting, the supernatant was filtered through 70 μm nylon cell strainer (Falcon). Collagenase treated tissue which had lost its integrity (e.g., loose cells) was able to pass through the filter. The cell filtrate was collected in a 50 mL tube (Falcon) and then centrifuged at 1,500 rpm for 5 minutes. Two thirds of the supernatant was discarded and the pellet washed with 10 ml of sterile PBS (1×). The resuspended cells were again centrifuged at 1,500 rpm for 5 minutes and, after removal of two-thirds of the supernatant, washed with 10 ml of sterile PBS (1×). The cells were again centrifuged at 1,500 rpm for 5 minutes and then resuspended in DMEM (containing 10% FBS). The resuspended cells were then transferred to four uncoated 25 cm² flasks and cultured for four days at 37° C. with 5% $CO_2$. The cells were then transferred into two uncoated 185 cm² flasks. The cells were cultured for two weeks and then collected, washed and resuspended in a cryopreservative media of DMEM, FBS and DMSO in a 5:4:1 ratio. The cells were aliquoted in to cryovials containing 1 mL of cell suspension at $4 \times 10^5$ cells/mL. The cells were held in vapor phase liquid nitrogen storage.

What is claimed is:

1. A method for preventing or retarding degeneration of intervertebral disc at an intervertebral disc defect site of a mammal comprising:
   a) inserting a gene encoding a protein having interverte-bral disc regenerating function into a mammalian cell to provide a transduced mammalian cell, and
   b) transplanting the transduced mammalian cell into the intervertebral disc defect site,
   wherein the protein is a TGF-B superfamily protein, and
   wherein the mammalian cell is a human embryonic kid-ney cell.

2. The method according to claim 1, wherein said gene encodes TGF-ß1.

3. The method according to claim 1, wherein the mam-malian cell is allogeneic relative to the mammal.

4. The method according to claim 1, wherein the mammal is human.

5. A method of treating degenerated or injured interver-tebral disc in a patient in need thereof, comprising employ-ing the method according to claim 1 to the patient.

6. A method for preventing or retarding degeneration of intervertebral disc at an intervertebral disc defect site of a mammal comprising:
   a) inserting a gene encoding a protein having interverte-bral disc regenerating function into a first mammalian cell to produce a transduced first mammalian cell, and
   b) transplanting a mixture of the transduced first mam-malian cell of a) and unmodified a second mammalian cell into the intervertebral disc defect site,
   wherein the protein is a TGF-ß superfamily protein, and
   wherein said first mammalian cell is a human embryonic kidney cell, and said second mammalian cell is a chondrocyte.

7. The method according to claim 6, wherein the chon-drocyte is a non-disc chondrocyte or juvenile chondrocyte.

8. The method according to claim 6, wherein the chon-drocyte is a primed chondrocyte.

9. The method according to claim 6, wherein the first and/or second mammalian cell is allogeneic relative to the mammal.

10. A method of treating degenerated or injured interver-tebral disc in a patient in need thereof, comprising employ-ing the method according to claim 6 to the patienta.

11. The method according to claim 6, wherein said gene encodes TGF-ß1.

* * * * *